United States Patent [19]

Hunkeler et al.

[11] 4,353,827
[45] Oct. 12, 1982

[54] DIAZEPINE DERIVATIVES

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 349,801

[22] Filed: Feb. 18, 1982

[30] Foreign Application Priority Data

Feb. 27, 1981 [CH] Switzerland ............. 1338/81
Feb. 27, 1981 [CH] Switzerland ............. 1339/81
Feb. 27, 1981 [CH] Switzerland ............. 1341/81
Feb. 27, 1981 [CH] Switzerland ............. 1342/81
Jun. 4, 1981 [CH] Switzerland ............. 3675/81
Dec. 11, 1981 [CH] Switzerland ............. 7934/81

[51] Int. Cl.³ .............. C07D 513/22; C07D 471/14; C07D 471/22
[52] U.S. Cl. ............. 260/239.3 P; 260/239.3 T; 424/256; 424/273 R
[58] Field of Search .................. 260/239.3 P

[56] References Cited
U.S. PATENT DOCUMENTS
4,316,832  2/1982  Gerecke et al. ............. 260/239.3 T Primary Examiner—Robert T. Bond
Attorney, Agent, or Firm—Jon S. Saxe; Bernard S. Leon; Frank P. Hoffman

[57] ABSTRACT

There is provided compounds which exhibit pronounced anticonvulsive and anxiolytic activities of the formula

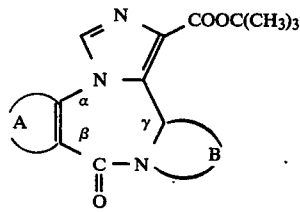

I wherein A together with the two carbon atoms denoted as α and β is the group

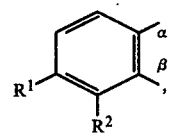

(a)

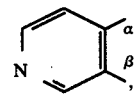

(b)

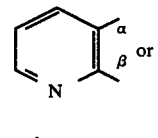

(c)

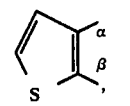

(d)

B is dimethylene, trimethylene or propenylene, $R^1$ is hydrogen, halogen, trifluoromethyl, amino, nitro, cyano or lower alkyl and $R^2$ is hydrogen, halogen, trifluoromethyl, amino, nitro, cyano, lower alkyl, lower alkoxy, lower alkylthio, lower alkylsulphinyl or lower alkylsulphonyl, and the carbon atom denoted as γ has the (S)—or (R,S)—configuration, and the pharmaceutically acceptable acid addition salts thereof.

21 Claims, No Drawings

DIAZEPINE DERIVATIVES

DESCRIPTION OF THE INVENTION

The present invention is concerned with imidazodiazepines. More particularly, the invention is concerned with tetracyclic imidazodiazepines of the formula

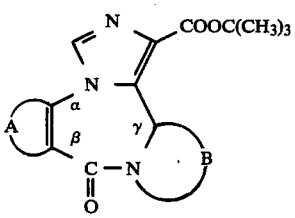   I wherein A together with the two carbon atoms denoted as α and β is the group

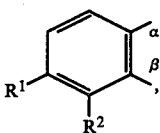   (a)

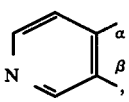   (b)

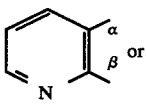   (c)

   (d)

B is dimethylene, trimethylene or propenylene, $R^1$ is hydrogen, halogen, trifluoromethyl, amino, nitro, cyano or lower alkyl and $R^2$ is hydrogen, halogen, trifluoromethyl, amino, nitro, cyano, lower alkyl, lower alkoxy, lower alkylthio, lower alkylsulphinyl or lower alkylsulphonyl, and the carbon atom denoted as γ has the (S)— or (R,S)—configuration, and pharmaceutically acceptable acid addition salts thereof.

These compounds are novel and possess valuable pharmacodynamic properties. They can be used in the control or prevention of illnesses.

Objects of the present invention are compounds of formula I and pharmaceutically acceptable acid addition salts thereof per se and as pharmaceutically active substances, the manufacture of these compounds, medicaments containing a compound of formula I or a pharmaceutically acceptable acid addition salt thereof and the manufacture of such medicaments.

The terms "lower alkyl", "lower alkyl group" and the like denote saturated hydrocarbon groups, which can be straight-chain or branched-chain containing at most 7, preferably at most 4, carbon atoms such as methyl, ethyl, n-propyl, isopropyl, n-butyl, s-butyl, t-butyl and the like. The term "lower alkoxy" denotes lower alkyl groups linked via an oxygen atom such as, for example, methoxy, ethoxy, isopropoxy and the like. The term "lower alkylthio" denotes lower alkyl groups linked via a sulphur atom such as, for example, methylthio, ethylthio, isopropylthio and the like. The term "lower alkylsulphinyl" denotes lower alkyl groups linked via a sulphoxide group such as, for example, methylsulphinyl, ethylsulphinyl, isopropylsulphinyl and the like. The term "lower alkylsulphonyl" denotes lower alkyl groups linked via a sulphone group such as, for example, methylsulphonyl, ethylsulphonyl, isopropylsulphonyl and the like. The term "halogen" signifies fluorine, chlorine, bromine or iodine.

In a particular embodiment the present invention embraces compounds of formula I hereinbefore in which A and B are as above, $R^1$ is hydrogen, amino or halogen and $R^2$ is hydrogen, halogen, trifluoromethyl, lower alkyl, cyano, nitro, amino, lower alkoxy, lower alkylthio, lower alkylsulphinyl or lower alkylsulphonyl, and the carbon atom denoted as γ has the (S)— or (R,S)—configuration.

The symbol A preferably is the group (a) in which $R^1$ preferably is hydrogen or halogen and $R^2$ preferably is halogen, trifluoromethyl or lower alkyl. The symbol B preferably is dimethylene or trimethylene. The carbon atom denoted as γ preferably has the (S)—configuration.

Quite especially preferred compounds of formula I are:

t-Butyl (S)-12,12a-dihydro-9-oxo-8-trifluoromethyl-9H,11H-azeto[2,1-c]imidazo[1,5-a][1,4]-benzodiazepine-1-carboxylate, t-butyl (S)-12,12a-dihydro-8-methyl-9-oxo-9H,11H-azeto[2,1-c]imidazo[1,5-a][1,4]benzodiazepine-1-carboxylate, t-butyl (S)-8-chloro-7-fluoro-11,12,13,13a-tetrahydro-9-oxo-9H-imidazo[1,5-a]pyrrolo[2,1-c][1,4]benzodiazepine-1-carboxylate, t-butyl (S)-8-chloro-11,12,13,13a-tetrahydro-9-oxo-9H-imidazo[1,5-a]pyrrolo[2,1-c][1,4]benzodiazepine-1-carboxylate, t-butyl (S)-8-ethyl-11,12,13,13a-tetrahydro-9-oxo-9H-imidazo[1,5-a]pyrrolo[2,1-c][1,4]benzodiazepine-1-carboxylate, t-butyl (S)-11,12,13,13a-tetrahydro-9-oxo-8-trifluoromethyl-9-H-imidazo[1,5-a]pyrrolo[2,1-c][1,4]benzodiazepine-1-carboxylate, t-butyl (S)-8-bromo-11,12,13,13a-tetrahydro-9-oxo-9H-imidazo[1,5-a]pyrrolo[2,1-c][1,4]benzodiazepine-1-carboxylate, t-butyl (S)-11,12,13,13a-tetrahydro-8-iodo-9-oxo-9H-imidazo[1,5-a]pyrrolo[2,1-c][1,4]benzodiazepine-1-carboxylate, t-butyl (S)-8-chloro-12,12a-dihydro-9-oxo-9H,11H-azeto[2,1-c]imidazo[1,5-a][1,4]benzodiazepine-1-carboxylate and t-butyl (S)-11,12,13,13a-tetrahydro-8-methyl-9-oxo-9H-imidazo[1,5-a]pyrrolo[2,1-c][1,4]benzodiazepine-1-carboxylate.

Other compounds of formula I which are preferred are:

t-Butyl 8-chloro-11,13a-dihydro-9-oxo-9H-imidazo[1,5-a]pyrrolo[2,1-c][1,4]benzodiazepine-1-carboxylate, t-butyl (S)-10,11,12,12a-tetrahydro-8-oxo-8H-imidazo[5,1-c]pyrrolo[1,2-a]thieno[3,2-e][1,4]diazepine-1-carboxylate,
t-butyl (S)-11,12,13,13a-tetrahydro-9-oxo-9H-imidazo[1,5-a]pyrrolo[2,1-c][1,4]benzodiazepine-1-carboxylate,
t-butyl (S)-7-chloro-11,12,13,13a-tetrahydro-9-oxo-9H-imidazo[1,5-a]pyrrolo[2,1-c][1,4]benzodiazepine-1-carboxylate,
t-butyl (S)-8-amino-11,12,13,13a-tetrahydro-9-oxo-9H-imidazo[1,5a]pyrrolo[2,1-c][1,4]benzodiazepine-1-carboxylate,
t-butyl (S)-11,12,13,13a-tetrahydro-8-nitro-9-oxo-9H-imidazo[1,5-a]pyrrolo[2,1-c][1,4]benzodiazepine-1-carboxylate,
t-butyl (S)-8-cyano-11,12,13,13a-tetrahydro-9-oxo-9H-imidazo[1,5-a]pyrrolo[2,1-c][1,4]benzodiazepine-1-carboxylate,
t-butyl (S)-11,12,13,13a-tetrahydro-8-methylthio-9-oxo-9H-imidazo[1,5-a]pyrrolo[2,1-c][1,4]benzodiazepine-1-carboxylate,
t-butyl (S)-11,12,13,13a-tetrahydro-8-methylsulphonyl-9-oxo-9H-imidazo[1,5-a]pyrrolo[2,1-c][1,4]benzodiazepine-1-carboxylate,
t-butyl (S)-7-fluoro-11,12,13,13a-tetrahydro-9-oxo-9H-imidazo[1,5-a]pyrrolo[2,1-c][1,4]benzodiazepine-1-carboxylate and
t-butyl (S)-8-chloro-13,13a-dihydro-9-oxo-9H-imidazo[1,5-a]pyrrolo[2,1-c][1,4]benzodiazepine-1-carboxylate.

Further representative members of the class of compound defined by formula I are:
t-Butyl (S)-8-bromo-12,12a-dihydro-9-oxo-9H,11H-azeto[2,1-c]imidazo[1,5-a][1,4]benzodiazepine-1-carboxylate,
t-butyl (S)-12,12a-dihydro-8-iodo-9-oxo-9H,11H-azeto[2,1-c]imidazo[1,5-a][1,4]benzodiazepine-1-carboxylate,
t-butyl (S)-8-ethyl-12,12a-dihydro-9-oxo-9H,11H-azeto[2,1-c]imidazo[1,5-a][1,4]benzodiazepine-1carboxylate,
t-butyl (S)-8-chloro-7-fluoro-12,12a-dihydro-9-oxo-9H,11H-azeto[2,1-c]imidazo[1,5-a][1,4]benzodiazepine-1-carboxylate,
t-butyl (S)-11,12,13,13a-tetrahydro-8-methylsulphinyl-9-oxo-9H-imidazo[1,5-a]pyrrolo[2,1-c][1,4]benzodiazepine-1-carboxylate,
t-butyl (S)-11,12,13,13a-tetrahydro-8-methoxy-9-oxo-9H-imidazo[1,5-a]pyrrolo[2,1-c][1,4]benzodiazepine-1-carboxylate,
t-butyl 11,12,13,13a-tetrahydro-9-oxo-9H-imidazo[5,1-c]pyrido[3,2-e]pyrrolo[1,2-a][1,4]diazepine-1-carboxylate,
t-butyl 11,12,13,13a-tetrahydro-9-oxo-9H-imidazo[5,1-c]pyrido[4,3-e]pyrrolo[1,2-a][1,4]diazepine-1-carboxylate,
t-butyl (S)-7-amino-11,12,13,13a-tetrahydro-9-oxo-9H-imidazo[1,5-a]pyrrolo[2,1-c][1,4]benzodiazepine-1-carboxylate and
t-butyl (S)-7-amino-8-bromo-11,12,13,13a-tetrahydro-9-oxo-9H-imidazo[1,5-a]pyrrolo[2,1-c][1,4]benzodiazepine-1-carboxylate.

The imidazodiazepines of formula I and their pharmaceutically acceptable acid addition salts can be manufactured in accordance with the invention by
(a) reacting a compound of the formula

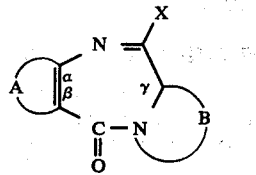

II wherein A and B is as above and X signifies a leaving group in the presence of a base with t-butyl isocyanoacetate, or (b) converting a carboxylic acid of the formula

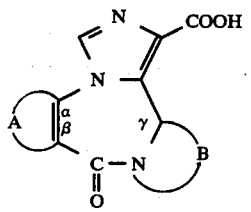

III wherein A and B are as above, with the proviso that $R^1$ and/or $R^2$ are not amino when A is the group (a), into the corresponding t-butyl ester, or (c) replacing the halogen atom in a compound of the formula

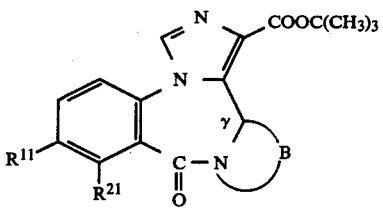

Ia wherein B is as above and either $R^{11}$ is halogen and $R^{21}$ is hydrogen, trifluoromethyl, amino, nitro, cyano or lower alkyl, or $R^{11}$ is hydrogen, trifluoromethyl, amino, nitro, cyano or lower alkyl and $R^{21}$ is halogen, by the cyano group or, when $R^{21}$ is halogen, also by a lower alkylthio group, or (d) replacing the amino group in a compound of the formula

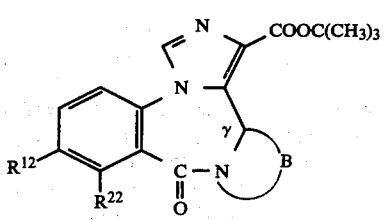

Ib wherein B is as above and either $R^{12}$ is amino and $R^{22}$ is hydrogen, halogen, trifluoromethyl, nitro, cyano or lower alkyl, or $R^{12}$ is hydrogen, halogen, trifluoromethyl, nitro, cyano or lower alkyl and $R^{22}$ signifies amino, by a hydrogen or halogen atom or a cyano or nitro group, or (e) halogenating a compound of the formula

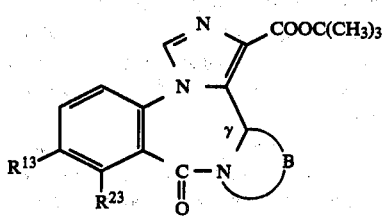

wherein B is as above and one of $R^{13}$ and $R^{23}$ is amino and the other is hydrogen, in the α-position to the amino group, or (f) oxidizing the lower alkylthio group to a lower alkylsulphinyl or lower alkylsulphonyl group or oxidizing the lower alkylsulphinyl group to a lower alkylsulphonyl group in a compound of the formula

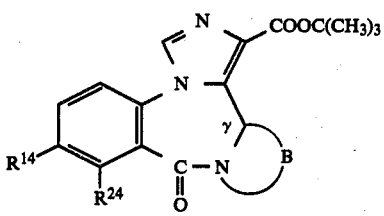

wherein B is as above, $R^{14}$ is hydrogen, halogen, trifluoromethyl, nitro, cyano or lower alkyl and $R^{24}$ is lower alkylthio or lower alkylsulphinyl, and (g) if desired, converting a compound of formula I obtained into a pharmaceutically acceptable acid addition salt.

In accordance with process variant (a), compounds of formula I can be manufactured from compounds of formula II and t-butyl isocyanoacetate. The leaving group denoted by X in formula II is, for example, a readily cleavable phosphinyl group, e.g. a group of the formula

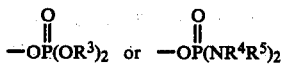

wherein $R^3$ is lower alkyl and $R^4$ and $R^5$ each are lower alkyl, allyl, phenyl or substituted phenyl or $R^4$ and $R^5$ together with the nitrogen atom are an unsubstituted or substituted heterocyclic ring with 3 to 8 members (such as morpholine), a halogen atom, an alkylthio group, an aralkylthio group, a N-nitrosoalkylamino group, an alkyloxy group, a mercapto group and the like (when X is a mercapto group, then the corresponding compound of formula II is the iminothiol form of the corresponding thiolactam). The reaction of a compound of formula II with t-butyl isocyanoacetate is carried out in an inert solvent such as dimethylformamide, hexamethylphosphoric acid triamide, dimethyl sulphoxide, tetrahydrofuran or any other suitable organic solvent and in the presence of a base which is sufficiently strongly basic to form the anion of the t-butyl isocyanoacetate. Suitable bases are alkali metal alkoxides such as sodium methoxide or potassium t-butoxide, alkali metal hydrides such as sodium hydride, alkali metal amides such as lithium amide or lithium diisopropylamide, tertiary amines such as triethylamine, and the like. The reaction is conveniently carried out at a temperature between about −40° C. and about room temperature.

In accordance with process variant (b), compounds of formula I can be manufactured by converting carboxylic acids of formula III into the corresponding t-butyl esters. This esterification can be carried out according to methods which are known per se and familiar to any person skilled in the art; it will, however, be appreciated that compounds of formula I which have an amino group as a structural element can not be manufactured in this manner. For example, a carboxylic acid of formula III can be converted with a suitable reagent (e.g. with thionyl chloride, phosphorus oxychloride, oxalyl chloride or the like) into the corresponding carboxylic acid chloride and this can be reacted with t-butanol in the presence of an acid-binding agent. Suitable acid-binding agents are primarily tertiary amines such as triethylamine, pyridine, quinuclidine or the like. Under certain circumstances the presence of a catalytic amount of 4-dimethylaminopyridine or a similar reactive amine can be advantageous. This esterification can be carried out in two separate steps, i.e. formation of the reactive carboxylic acid derivative and reaction thereof with t-butanol or in a so-called one-pot process, which is preferred. Suitable solvents are, for example, halogenated hydrocarbons such as methylene chloride, chloroform, 1,2-dichloroethane and the like, ethers such as diethyl ether, t-butyl methyl ether, tetrahydrofuran and the like, acetonitrile, dimethylformamide etc. The esterification is conveniently carried out at a temperature in the range of about −10° C. to the boiling point of the mixture.

It is, however, also possible to react a carboxylic acid chloride, obtained as described earlier, or a carboxylic acid imidazolide, which is readily accessible by reacting the free carboxylic acid of formula III with N,N′-carbonyldiimidazole, with sodium or potassium t-butoxide. Especially suitable solvents are ethers such as tetrahydrofuran and dioxan, dimethylformamide and the like. Thereby, depending on the solvent used, the reaction is carried out at a temperature in the range of about 0° C. to about 100° C., but preferably at room temperature.

In accordance with process variant (c), compounds of formula I in which A is the group (a) and either $R^1$ is cyano and $R^2$ is hydrogen, trifluoromethyl, amino, nitro, cyano or lower alkyl, or $R^1$ is hydrogen, trifluoromethyl, amino, nitro, cyano or lower alkyl and $R^2$ is cyano or lower alkylthio, can be manufactured by replacing the halogen atom in compounds of formula Ia by the cyano group or, when $R^{21}$ is halogen, also by a lower alkylthio group. Thereby, a corresponding bromo or iodo compound of formula Ia is preferably used as the starting material. The reaction can be carried out, for example, by reacting the compound of formula Ia in an inert organic solvent with copper (I) cyanide or a lower alkyl mercaptan in the presence of a base which is sufficiently strongly basic to form the corresponding anion from the mercaptan. Suitable solvents are, for example, dimethylformamide and the like. The temperature at which the reaction is carried out conveniently lies in a range of about room temperature to the boiling point of the reaction mixture. Suitable bases for the preparation of the anion from a lower alkyl mercaptan are, for example, a sodium or potassium alcoholate such as sodium ethanolate and potassium t-butanolate, sodium hydride and the like.

In accordance with process variant (d), the amino group in a compound of formula Ib can be replaced by a hydrogen or halogen atom or a cyano or nitro group. The replacement by a halogen atom or a cyano or nitro group can be carried out by converting the amino compound of formula Ib into a corresponding diazonium salt and reacting this, optionally without previous isolation, with a nitrite such as sodium nitrite, or with a halide (e.g. a chloride or bromide) or with a cyanide in the presence of a copper (I) salt. The presence of a copper (I) salt is not necessary for the manufacture of the corresponding iodides. Corresponding fluorides are conveniently manufactured via a corresponding diazonium tetrafluoroborate, for example by irradiation with UV light. These reactions are carried out in aqueous solutions at temperatures of about −10° C. to about room temperature.

The replacement of an amino group in a compound of formula Ib by the nitro group can, however, also be carried out by oxidizing a compound of formula Ib. Suitable oxidizing agents are, for example, peracids such as peracetic acid, trifluoroperacetic acid, m-chloroperbenzoic acid and perbenzoic acid and the like. As solvents there can be used, depending on the oxidizing agent used, carboxylic acids such as acetic acid etc., halogenated hydrocarbons such as methylene chloride, chloroform, 1,2-dichloroethane etc., or the like. As a rule, the oxidation is carried out at a temperature of about 0° C. to about room temperature.

The replacement of the amino group by a hydrogen atom can be carried out, for example, by reducing a corresponding diazonium salt, for example by heating in a cyclic ether such as tetrahydrofuran or dioxan or in dimethylformamide; thereby the reaction mixture is preferably heated at the boiling point. However, in an especially preferred embodiment an amine of formula Ib is reacted in a cyclic ether such as tetrahydrofuran or dioxan with t-butyl nitrite, preferably at the boiling point of the reaction mixture.

In accordance with process variant (e), a compound of formula Ic can be halogenated in the α-position to the amino group. Suitable halogenating agents are, for example, N-chlorosuccinimide, N-bromosuccinimide, N-chloroacetamide, N-bromoacetamide and the like. As solvents there are conveniently used inert organic solvents, for example halogenated hydrocarbons such as methylene chloride, 1,2-dichloroethane, chloroform and the like, dimethylformamide, dimethylacetamide, acetonitrile, ethers such as diethyl ether, tetrahydrofuran, dioxan and the like, etc. The halogenation can be carried out in a temperature range of about 0° C. to the boiling point of the mixture, a range of about room temperature to about 100° C. being preferred.

In accordance with process variant (f), the lower alkylthio or lower alkylsulphinyl group in a compound of formula Id can be oxidized. In the oxidation of a lower alkylthio group there is obtained, depending on the reaction conditions used, a corresponding alkylsulphinyl or alkylsulphonyl compound. Suitable oxidizing agents are, for example, peracids such as peracetic acid, trifluoroperacetic acid, m-chloroperbenzoic acid and perbenzoic acid, alkyl hydroperoxides such as t-butyl hydroperoxide, hydrogen peroxide and the like. As solvents there can be used, depending on the oxidizing agent used, carboxylic acids such as acetic acid etc., halogenated hydrocarbons such as methylene chloride, chloroform, 1,2-dichloroethane etc., aromatic hydrocarbons such as benzene, toluene and xylene or the like. As a rule, the oxidation is carried out at a temperature of about 0° C. to the boiling point of the mixture.

An additional optically active centre is obtained by the introduction of an alkylsulphinyl group; the present invention embraces all possible diastereoisomers and mixtures thereof.

In accordance with process variant (g), compounds of formula I can be converted into pharmaceutically acceptable acid addition salts. The manufacture of such pharmaceutically acceptable acid addition salts is carried out according to generally usual methods. The salts provided by the present invention are salts formed with inorganic acids and organic acids: for example, hydrochlorides, hydrobromides, sulphates, methanesulphonates, p-toluenesulphonates, oxalates and the like.

The compounds of formula II used as starting materials can be prepared starting from compounds of the general formula

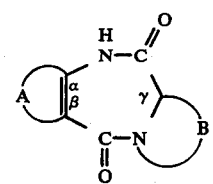

IV wherein A and B are as above, according to methods known per se; see, for example, Belgian Patent Specifications Nos. 802 233, 833 249 and 865 653, U.S. Pat. No. 3,681,341 and J. Org. Chemistry 29, 231 (1964) which are incorporated herein for reference.

Various Examples hereinafter contain detailed information concerning the preparation of compounds of formula II from compounds of formula IV.

The compounds of general formula IV, in turn, are known or can be prepared readily according to methods known per se. Compounds of formula IV in which A is the group (a) or (d) can be prepared, for example, by reacting a corresponding carboxylic acid anhydride of the formula

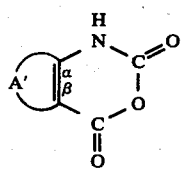

V wherein A' is the group (a) or (d), with the proviso that $R^1$ and/or $R^2$ are not amino when A' is the group (a), with an amino acid of the formula

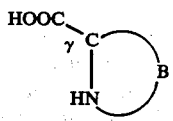

VI wherein B is as above.

The compounds of formula IV in which A is the group (a) or (d) can, however, also be prepared starting from compounds of the formula

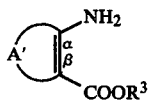 VII wherein $R^3$ is lower alkyl and A' is as above, for example by reaction with a reactive derivative of a carboxylic acid of the formula

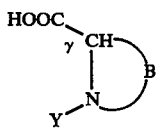 VIII wherein Y is a protecting group and B is as above, for example a carboxylic acid chloride or the like. After removing the protecting group denoted by Y from a thus-obtained compound of the formula

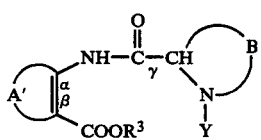 IX wherein A', B, $R^3$ and Y are as above, and cyclization, for example by heating the substance obtained to a temperature of about 100° to about 300° C. for a short time, there is obtained the desired compound of formula IV.

Compounds of formula IV, in which A is the group (b) or (c) can be prepared by reacting a compound of the formula

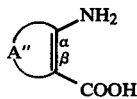 X wherein A'' is the group (b) or (c), in an inert organic solvent such as dimethylformamide, tetrahydrofuran, dioxan or the like in the presence of N,N'-carbonyldiimidazole with a compound of the formula

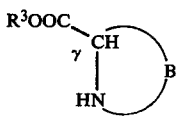 XI wherein B and $R^3$ are as above.

This reaction is preferably carried out as a "one-pot process", i.e. the carboxylic acid imidazolide formed in a first step is not isolated, but is reacted directly with a compound of formula XI and cyclizing the substance obtained, for example by heating to a temperature of about 100° to about 300° C. for a short time.

Compounds of the formula

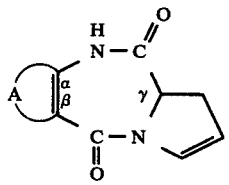 IVa wherein A is as above, can also be manufactured by eliminating in a manner known per se the leaving group denoted by X' in a compound of the formula

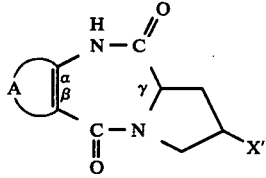 XII wherein A is as above and X' is a leaving group.

As leaving groups there come into consideration, for example, sulphonic acid groups such as methanesulphonyloxy, p-toluenesulphonyloxy and the like, halogen atoms such as chlorine, bromine and iodine, or the like. The elimination is carried out using a base such as sodium hydride in an inert organic solvent such as dimethylformamide.

Compounds of formula XII can be prepared, for example, in analogy to the preparation of compounds of formula IV from compounds of formulae V and VI, or from compounds of formulae X and XI.

Compounds of formula IV in which A is the group (a), one of $R^1$ and $R^2$ is halogen and the other is hydrogen, trifluoromethyl, amino, nitro, cyano or lower alkyl can be converted into corresponding cyano or alkylthio compounds by treatment with copper (I) cyanide or a lower alkyl mercaptan in the presence of a base. Corresponding lower alkylsulphinyl and lower alkylsulphonyl compounds can be obtained by oxidizing corresponding lower alkylthio compounds. A further possibility for the modification of compounds of formula IV in which A signifies the group (a) comprises halogenating such a compound, wherein one of $R^1$ and $R^2$ is amino and the other is hydrogen, in the α-position to the amino group. Furthermore, in a compound of formula IV in which A is the group (a), one of $R^1$ and $R^2$ is amino and the other is hydrogen, halogen, trifluoromethyl, nitro, cyano or lower alkyl, the amino group can be cleaved off, for example by reduction of a corresponding diazonium salt or the amino group can be replaced by a halogen atom or the cyano or nitro group via a corresponding diazonium salt, or the amino group can be oxidized to the nitro group. Finally, a compound of formula IV in which A is the group (a) and $R^1$ and $R^2$ are hydrogen can be nitrated to give a corresponding compound of formula IV in which $R^1$ is nitro and $R^2$ is hydrogen, or a corresponding compound in which one of $R^1$ and $R^2$ is nitro can be reduced to the corresponding amino compound.

The compounds of formula III used as starting materials can be prepared readily by hydrolyzing the ester group in compounds of the formula

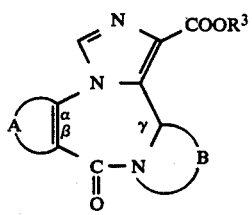 XIII wherein A, B and $R^3$ are as above, according to methods which are known per se and familiar to any person skilled in the art.

The compounds of formula XIII can be prepared by reacting a compound of formula II in the presence of a base with an isocyanoacetic ester of the formula $$CN-CH_2-COOR^3 \quad\quad XIV$$

wherein $R^3$ is as above, in analogy to process variant (a).

As mentioned earlier, the compounds of formula I are novel and have extremely valuable pharmacodynamic properties. They exhibit only a low toxicity and it has been shown that they have a pronounced anticonvulsive and anxiolytic activity. The anxiolytic activity can be demonstrated experimentally in the animal test described hereinafter.

The test apparatus is a one-touch Skinner box with a feed pellet dispenser.

During 3 one-hour preliminary tests (on three different days) starved female rats (180–230 g) are trained to press the key of the feed pellet dispenser in order to receive feed pellets each weighing 45 mg (each key press is rewarded); in the third preliminary test the rats attain a rate of 150–200 key operations per hour.

In a fourth preliminary test each pellet reward brought about by key pressing is combined with a short electric foot-shock (1.0 mA). The rats which are confronted with this conflict situation initially operate the press-key for about a further 5–10 times and then stop completely from fright.

In a fifth preliminary test the rats can press the key of the feed pellet dispenser again without accompanying foot-shock, whereby again a rate of 150–200 key operations per hour is attained.

In a sixth preliminary test a selection of the test animals is carried out. 10 mg/kg of chlordiazepoxide are administered perorally to the test animals 0.5 hour before the beginning of this preliminary test; each pellet reward is again combined with a foot-shock (conflict). Only rats which in this preliminary test attain a rate of 20–50 key operations (compare the 5–10 key operations in the fourth preliminary test) are retained as suitable test animals for the testing of potential anxiolytics. The elimination rate in this preliminary test amounts to 5%.

In the main test 8 rats are usually used per substance and per dosage for the testing of the potential anxiolytics. An untreated control group is not necessary, since each animal serves as its own control. The test substances which are dissolved or suspended in a mixture of 10 ml of distilled water and 2 drops of Tween 80 (polyoxyethylene sorbitan monooleate) are administered to the animals with the aid of a probang 0.5 hour before the one-hour main test. During the main test, in which with each key press the pellet reward is combined with a foot-shock (conflict), the rate of key operations per hour is registered.

The first significant anxiolytically active dosage is determined with the Wilcoxon Test (comparison of pairs) by directly comparing the number of key operations in the main test (foot-shock, after pre-treatment with test substance) with the number of key operations in the control test (foot-shock, after pre-treatment with sodium chloride solution).

The following Table contains, for representative compounds of formula I, the first significant anxiolytically active dosage (FSD) determined in the above test, as well as details concerning their acute toxicity in the case of single oral administration to mice ($LD_{50}$ in mg/kg).

TABLE

| | | Compound of formula I | | | FSD in | $LD_{50}$ in |
|---|---|---|---|---|---|---|
| A | $R^1$ | $R^2$ | B | Configuration | mg/kg | mg/kg p.o. |
| (a) | H | Cl | $-(CH_2)_3-$ | (S) | 0.625 | 1250 |
| (a) | H | H | $-(CH_2)_3-$ | (S) | 10 | 2500 |
| (a) | H | Cl | $-(CH_2)_2-$ | (S) | 0.625 | 5000 |
| (a) | F | H | $-(CH_2)_3-$ | (S) | 5 | |
| (a) | H | $-SO_2CH_3$ | $-(CH_2)_3-$ | (S) | 5 | |
| (a) | H | $-SCH_3$ | $-(CH_2)_3$ | (S) | 1.25 | |
| (a) | H | $-CH_3$ | $-(CH_2)_3$ | (S) | 1.25 | 2500 |
| (d) | — | — | $-(CH_2)_3$ | (S) | 10 | |
| (a) | H | Cl | $\gamma$-CH=CH-CH_2- | (R,S) | 10 | |
| (a) | H | $-CH_3$ | $-(CH_2)_2-$ | (S) | 2.5 | |
| (a) | H | I | $-(CH_2)_3-$ | (S) | <0.625 | >4000 |

The compounds of formula I and their pharmaceutically acceptable acid addition salts can be used as medicaments, for example in the form of pharmaceutical preparations. The pharmaceutical preparations can be administered orally (e.g. in the form of tablets, coated tablets, dragées, hard and soft gelatine capsules, solutions, emulsions or suspensions). The administration can, however, also be carried out rectally (e.g. in the form of suppositories) or parenterally (e.g. in the form of injection solutions).

For the manufacture of pharmaceutical preparations, the compounds of formula I and their pharmaceutically acceptable acid addition salts can be processed with pharmaceutical inert, inorganic or organic carriers. Examples of carriers which can be used for tablets, coated tablets, dragées and hard gelatine capsules are lactose, maize starch or derivatives thereof, talc, stearic acid or its salts and the like. Suitable carriers for soft gelatine capsules are, for example, vegetable oils, waxes, fats, semi-solid and liquid polyols and the like; depending on the nature of the active substance no carriers are, however, generally necessary in the case of soft gelatine capsules. Suitable carriers for the manufacture of solutions and syrups are, for example, water, polyols, saccharose, invert sugar, glucose and the like. Suitable carriers for injections solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, colouring agents, flavouring agents, salts, for varying the osmotic pressure, buffers, coating agents or antioxidants. They can also contain still other therapeutically valuable substances.

As mentioned earlier, medicaments containing a compound of formula I or a pharmaceutically acceptable acid addition salt thereof are likewise an object of the present invention as is a process for the manufacture of such medicaments which comprises bringing one or more compounds of formula I or pharmaceutically acceptable acid addition salts thereof and, if desired, one or more other therapeutically valuable substances into a galenical administration form. As mentioned earlier, the compounds of formula I and their pharmaceutically acceptable acid addition salts can be used in the control or prevention of illnesses, especially in the control of convulsions and anxiety states. The dosage can vary within wide limits and is, of course, fitted to the individual requirements in each particular case. In general, in the case of oral administration a daily dosage of about 0.1 mg to 100 mg should be appropriate.

The following Examples illustrate the present invention, but in no way are intended to limit its extent. All temperatures are given in degrees Centigrade.

EXAMPLE 1

(a) 10 g (50.6 mmol) of 6-chloroisatoic acid anhydride are stirred at 110° for 2 hours with 5.82 g (50.6 mmol) of L-proline in 80 ml of dimethyl sulphoxide. The solution is evaporated and the residue is crystallized from ethyl acetate. There is obtained (S)-6-chloro-1,2,3,11a-tetrahydro-5H-pyrrolo[2,1-c][1,4]benzodiazepine-5,11(10H)-dione of melting point 271°–276°.

(b) A suspension of 1.3 g (29.8 mmol) of sodium hydride (55 percent oil dispersion) in 40 ml of dry dimethylformamide is treated at 20° to 30° while stirring with 6.8 g (27.1 mmol) of (S)-6-chloro-1,2,3,11a-tetrahydro-5H-pyrrolo[2,1-c][1,4]benzodiazepine-5,11(10H)-dione, the mixture is stirred in the above temperature range for 45 minutes and then at −35° 4.4 ml (27.1 mmol) of diethylchlorophosphate are added dropwise thereto.

Separately, 3.0 g (27.1 mmol) of potassium t-butylate are dissolved in 9.0 ml of dry dimethylformamide, cooled in an acetone/dry-ice bath, treated with 3.9 g (27.1 mmol) of t-butyl isocyanoacetate and the solution obtained is added dropwise at −15° to the mixture obtained according to the preceding paragraph. The mixture is warmed to 15°, neutralized with 1.5 ml of glacial acetic acid, poured into 100 ml of water and extracted four times with methylene chloride. The methylene chloride solution is washed twice with water, dried over magnesium sulphate, evaporated and the crude product obtained is chromatographed on silica gel using ethyl acetate for the elution. By recrystallization from ethyl acetate/n-hexane there is obtained t-butyl (S)-8-chloro-11,12,13,13a-tetrahydro-9-oxo-9H-imidazo[1,5-a]pyrrolo[2,1-c][1,4]benzodiazepine-1-carboxylate of melting point 151°–152° (a second modification melts at 216°–217°).

EXAMPLE 2

(a) A mixture of 4.8 g (24.3 mmol) of 6-chloroisatoic acid anhydride, 2.83 g (25 mmol) of (L)-3,4-dehydroproline and 20 ml of dimethyl sulphoxide is stirred at 100° for 1.25 hours, subsequently poured into 200 ml of water and extracted three times with ethyl acetate. The ethyl acetate solution is washed once with water, dried over magnesium sulphate, filtered and evaporated. The residue obtained is chromatographed on silica gel and subsequently recrystallized from ethyl acetate, there being obtained (S)-6-chloro-3,11a-dihydro-5H-pyrrolo[2,1-c][1,4]benzodiazepine-5,11(10H)-dione of melting point 254°–256°.

(b) A suspension of 1.9 g (44.6 mmol) of sodium hydride (55 percent oil dispersion) in 80 ml of dry dimethylformamide is treated at −10° while stirring with 10.0 g (40.2 mmol) of (S)-6-chloro-3,11a-dihydro-5H-pyrrolo[2,1-c][1,4]benzodiazepine-5,11(10H)-dione, the mixture is stirred for 1 hour and subsequently at −35° 7.7 ml (44.6 mmol) of diethylchlorophosphate are added dropwise thereto.

Separately, 4.9 g (44.4 mmol) of potassium t-butylate are dissolved in 15 ml of dry dimethylformamide, cooled in an acetone/dry-ice bath, treated with 6.31 g (44.6 mmol) of t-butyl isocyanoacetate and the solution obtained is added dropwise at −15° to the mixture obtained according to the preceding paragraph. The mixture is left to warm to 15°, neutralized with 2.5 ml of glacial acetic acid, poured into 150 ml of water and extracted three times with methylene chloride. The organic extracts are washed twice with water, dried over magnesium sulphate and evaporated. The crude product obtained is chromatographed on silica gel using ethyl acetate for the elution. After recrystallization from ethyl acetate/n-hexane, there is obtained t-butyl 8-chloro-11,13a-dihydro-9-oxo-9H-imidazo[1,5-a]pyrrolo[2,1-c][1,4]benzodiazepine-1-carboxylate of melting point 227°–229°.

EXAMPLE 3

(a) 11.3 g (0.057 mol) of 6-chloroisatoic acid anhydride and 5.78 g (0.057 mol) of L-azetidinecarboxylic acid are heated to 125° for 2 hours in 50 ml of dimethyl sulphoxide. Subsequently, the mixture is evaporated to dryness in a high vacuum and the residue obtained is heated to 150° for 2 hours. By chromatography on silica gel using ethyl acetate for the elution there is obtained (S)-5-chloro-1,10a-dihydroazeto[2,1-c][1,4]benzodiazepine-4,10(2H,9H)-dione of melting point 225°–228°.

(b) A suspension of 0.47 g (10.8 mmol) of sodium hydride (55 percent oil dispersion) in 10 ml of dry dimethylformamide is treated at −15° while stirring with 2.12 g (9.0 mmol) of (S)-5-chloro-1,10a-dihydroazeto[2,1-c][1,4]benzodiazepine-4,10(2H,9H)-dione, the mixture is stirred for a further 1 hour and subsequently at −35° 1.8 ml (10.8 mmol) of diethylchlorophosphate are added dropwise thereto.

Separately, 1.18 g (10.8 mmol) of potassium t-butylate are dissolved in 8 ml of dry dimethylformamide, cooled in an acetone/dry-ice bath, treated with 1.52 g (10.8 mmol) of t-butyl isocyanoacetate and the solution obtained is added dropwise at −15° to the mixture obtained according to the preceding paragraph. The mixture is left to warm to 10°, neutralized with 0.6 ml of glacial acetic acid, poured into 80 ml of water and extracted three times with chloroform. The chloroform solution is washed twice with water, dried over magnesium sulphate and evaporated. The crude product obtained is chromatographed on silica gel using ethyl acetate for the elution and subsequently recrystallized from ethyl acetate, there being obtained t-butyl (S)-8-chloro-12,12a-dihydro-9-oxo-9H,11H-azeto[2,1-c]imidazo[1,5-a][1,4]benzodiazepine-1-carboxylate of melting point 235°–236°.

EXAMPLE 4

(a) A mixture of 175 g (0.93 mol) of methyl 3-amino-2-thiophenecarboxylate hydrochloride, 1.8 l of n-butanol and 77 g of sodium hydroxide is heated to boiling under reflux for 30 minutes and the suspension obtained is concentrated. The resulting mixture of the sodium salt of 3-amino-2-thiophenecarboxylic acid and sodium chloride is treated with 800 ml of water, 280 ml of concentrated hydrochloric acid and 230 ml of tetrahydrofuran and at 15° to 25° phosgene is conducted through this mixture for 2.5 hours and subsequently air is conducted through the mixture for 15 minutes. The precipitated solid material is filtered off under suction, washed with water and dried. There is obtained 2H-thieno[3,2-d][1,3]oxazine-2,4(1H)-dione of melting point 220°–221°.

(b) A solution of 34.3 g (202 mmol) of 2H-thieno[3,2-d][1,3]oxazine-2,4(1H)-dione and 23.3 g (202 mmol) of L-proline in 200 ml of dimethyl sulphoxide is stirred at 110° for 1 hour, the brown solution obtained is poured into 2 l of water and stirred at room temperature overnight. The precipitated product is filtered off under suction, dried in vacuo and washed with about 200 ml of boiling ethyl acetate. There is thereby obtained (S)-5a,6,7,8-tetrahydro-5H-pyrrolo[1,2a]thieno[3,2-e][1,4]diazepine-5,10(4)-dione of melting point 244°–247°.

(c) A suspension of 6.66 g (30 mmol) of (S)-5a,6,7,8-tetrahydro-5H-pyrrolo[1,2-a]thieno[3,2-e][1,4]diazepine-5,10(4H)-dione in 30 ml of dry dimethylformamide is treated at 0° while stirring with 1.15 g (30 mmol) of sodium hydride (55 percent oil dispersion), the mixture is subsequently stirred at the above temperature for 1 hour and then at −30° 4.3 ml (30 mmol) of diethylchlorophosphate are added dropwise thereto.

Separately, 3.37 g (30 mmol) of potassium t-butylate are dissolved in 10 ml of dry dimethylformamide, cooled in an acetone/dry-ice bath, treated with 4.23 g (30 mmol) of t-butyl isocyanoacetate and the solution obtained is added dropwise at −15° to the mixture obtained according to the preceding paragraph. The mixture is left to warm to 10°, neutralized with 3.3 ml of glacial acetic acid, poured into 300 ml of water and extracted three times with chloroform. The chloroform solution is washed four times with water, dried over magnesium sulphate and evaporated. The partly crystalline residue is recrystallized twice from ethyl acetate and yields t-butyl (S)-10,11,12,12a-tetrahydro-8-oxo-8H-imidazo[5,1-c]pyrrolo[1,2-a]thieno[3,2-e][1,4]diazepine-1-carboxylate of melting point 226°–227°.

EXAMPLE 5

A suspension of 10.8 g (50.0 mmol) of (S)-1,2,3,11a-tetrahydro-5H-pyrrolo[2,1-c][1,4]benzodiazepine-5,11-(10H)-dione in 50 ml of dry dimethylformamide is treated at 0° while stirring with 1.92 g (50 mmol) of sodium hydride (55 percent oil dispersion), the mixture is stirred at the above temperature for a further 40 minutes and subsequently at −25° 7.3 ml (50 mmol) of diethylchlorophosphate are added dropwise thereto.

Separately, 5.6 g (50 mmol) of potassium t-butylate are dissolved in 15 ml of dry dimethylformamide, cooled in an acetone/dry-ice bath, treated with 7.0 g (50 mmol) of t-butyl isocyanoacetate and the thus-obtained solution is added dropwise at −15° to the mixture obtained according to the preceding paragraph. The mixture is left to warm to 10°, neutralized with 5.0 ml of glacial acetic acid, poured into 500 ml of water and stirred for 0.5 hours. The precipitated material is filtered off under suction, washed with water, dried in vacuo and recrystallized from ethyl acetate. There is obtained t-butyl (S)-11,12,13,13a-tetrahydro-9-oxo-9H-imidazo[1,5-a]pyrrolo[2,1-c][1,4]benzodiazepine-1-carboxylate of melting point 237°–238°.

EXAMPLE 6

(a) A solution of 13.6 g (0.0768 mol) of 6-methylisatoic acid anhydride and 8.8 g (0.0768 mol) of L-proline in 75 ml of dimethyl sulphoxide is heated at 110° for 1 hour. Subsequently, the mixture is evaporated to dryness in a high vacuum and the residue is recrystallized from ethyl acetate with the addition of active carbon. There is obtained (S)-1,2,3,11a-tetrahydro-6-methyl-5H-pyrrolo[2,1-c][1,4]benzodiazepine-5,11(10H)-dione of melting point 212°–214°.

(b) A suspension of 2.51 g (57.5 mmol) of sodium hydride (55 percent oil dispersion) in 80 ml of dry dimethylformamide is treated at −20° while stirring with 11.5 g (50 mmol) of (S)-1,2,3,11a-tetrahydro-6-methyl-5H-pyrrolo[2,1-c][1,4]benzodiazepine-5,11(10H)-dione, the mixture is stirred for 1 hour and the solution obtained is treated dropwise at −40° with 8.6 ml (57.5 mmol) of diethylchlorophosphate.

Separately, 6.45 g (57.5 mmol) of potassium t-butylate are dissolved in 15 ml of dry dimethylformamide, cooled in an acetone/dry-ice bath and treated with 8.12 g (57.5 mmol) of t-butyl isocyanoacetate and the thus-obtained solution is added dropwise at −15° to the mixture obtained according to the preceding paragraph. The mixture is left to warm to 10°, neutralized with 3.3 ml of glacial acetic acid, poured into 300 ml of water and extracted four times with methylene chloride. The methylene chloride solution is washed twice with water, dried over magnesium sulphate and evaporated. The residue is chromatographed on silica gel using ethyl acetate containing 25% n-hexane for the elution. After recrystallization from ethyl acetate, there is obtained t-butyl (S)-11,12,13,13a-tetrahydro-8-methyl-9-oxo-9H-imidazo[1,5-a]pyrrolo[2,1-c][1,4]benzodiazepine-1-carboxylate of melting point 192°–194°.

EXAMPLE 7

A suspension of 2.40 g (55 mmol) of sodium hydride (55 percent oil dispersion) in 80 ml of dry dimethylformamide is treated at −10° while stirring with 12.0 g (47.9 mmol) of (S)-7-chloro-1,2,3,11a-tetrahydro-5H-pyrrolo[2,1-c][1,4]benzodiazepine-5,11(10H)-dione, the mixture is stirred for 1 hour and the solution obtained is treated dropwise at −40° with 9.2 ml (55 mmol) of diethylchlorophosphate.

Separately, 6.0 g (55 mmol) of potassium t-butylate are dissolved in 150 ml of dry dimethylformamide, cooled in an acetone/dry-ice bath, treated with 7.74 g (55 mmol) of t-butyl isocyanoacetate and the thus-obtained solution is added dropwise at −15° to the mixture obtained according to the preceding paragraph. The cooling bath is removed, the mixture is stirred for a further 1 hour, subsequently neutralized with 3.1 ml of glacial acetic acid, poured into 150 ml of water and extracted four times with methylene chloride. The organic solution is washed twice with water, dried over magnesium sulphate and the solvent is distilled off. The residue is chromatographed on silica gel using methylene chloride containing 5% ethyl acetate for the elution and recrystallized from ethyl acetate. There is obtained t-butyl (S)-7-chloro-11,12,13,13a-tetrahydro-9-oxo-9H-imidazo[1,5-a]pyrrolo[2,1-c][1,4]benzodiazepine-1-carboxylate of melting point 157°–158°.

EXAMPLE 8

(a) 9.2 g (0.038 mol) of 6-bromoisatoic acid anhydride and 4.6 g (0.040 mol) of L-proline in 55 ml of dimethyl sulphoxide are heated at 70° for 1 hour, the solvent is removed in a high vacuum and the oil obtained is heated at 170° for 15 minutes. The crude product is purified by chromatography on silica gel using a mixture of chloroform and methanol (20:1) as the elution agent. There is obtained (S)-6-bromo-1,2,3,11a-tetrahydro-5H-pyrrolo[2,1-c][1,4]benzodiazepine-5,11(10H)-dione which melts at 221°–224° after recrystallization from chloroform/hexane.

(b) A solution of 9.94 g (33.7 mmol) of (S)-6-bromo-1,2,3,11a-tetrahydro-5H-pyrrolo[2,1-c][1,4]benzodiazepine-5,11(10H)-dione in 30 ml of dry dimethylformamide is treated at −20° to −10° while stirring with 1.62 g (37 mmol) of sodium hydride (55 percent oil dispersion), the mixture is stirred in the above temperature range for a further 1.25 hours and then at −40° 5.5 ml (37 mmol) of diethylchlorophosphate are added dropwise thereto.

Separately, 4.15 g (37 mmol) of potassium t-butylate are dissolved in 10 ml of dry dimethylformamide, cooled in an acetone/dry-ice bath, treated with 5.22 g (37 mmol) of t-butyl isocyanoacetate and the solution obtained is added dropwise at −15° to the mixture obtained according to the preceding paragraph. The mixture is left to warm to 10°, neutralized with 2.1 ml of glacial acetic acid, poured into 150 ml of water and extracted three times with methylene chloride. The methylene chloride solution is washed twice with water, dried over magnesium sulphate and evaporated. The crude product obtained is chromatographed on silica gel using ethyl acetate for the elution. By recrystallization from ethyl acetate there is obtained t-butyl (S)-8-bromo-11,12,13,13a-tetrahydro-9-oxo-9H-imidazo[1,5-a]pyrrolo[2,1-c][1,4]benzodiazepine-1-carboxylate of melting point 206°–208°.

EXAMPLE 9

(a) 14.5 g (0.050 mol) of 6-iodoisatoic acid anhydride and 6.6 g (0.058 mol) of L-proline in 50 ml of dimethyl sulphoxide are warmed to 70° for 30 minutes, the solvent is removed in a high vacuum and the oil obtained is heated at 170° for 15 minutes. The crude product is purified by chromatography on silica gel using methylene chloride and a mixture of methylene chloride and ethyl acetate for the elution. There is obtained (S)-1,2,3,11a-tetrahydro-6-iodo-5H-pyrrolo[2,1-c][1,4]benzodiazepine-5,11(10H)-dione which melts at 212°–215° after recrystallization from methanol.

(b) A solution of 10.0 g (29.2 mmol) of (S)-1,2,3,11a-tetrahydro-6-iodo-5H-pyrrolo[2,1-c][1,4]benzodiazepine-5,11(10H)-dione in 30 ml of dry dimethylformamide is treated at −20° while stirring with 1.4 g (32.1 mmol) of sodium hydride (55 percent oil dispersion), the mixture is stirred at the above temperature for a further 1 hour and subsequently at −45° 4.8 ml (32.1 mmol) of diethylchlorophosphate are added dropwise thereto.

Separately, 3.6 g (32.1 mmol) of potassium t-butylate are dissolved in 8 ml of dry dimethylformamide, cooled in an acetone/dry-ice bath, treated with 4.5 g (32.1 mmol) of t-butyl isocyanoacetate and the solution obtained is added dropwise at −20° to the mixture obtained according to the preceding paragraph. The mixture is stirred at −20° for a further 15 minutes, neutralized with 1.9 ml of glacial acetic acid, poured into 150 ml of water and extracted three times with methylene chloride. The organic extracts are washed twice with water, dried over magnesium sulphate and evaporated. The crude product obtained is chromatographed on silica gel using ethyl acetate containing 30% n-hexane for the elution and subsequently recrystallized from ethyl acetate. There is obtained t-butyl (S)-11,12,13,13a-tetrahydro-8-iodo-9-oxo-9H-imidazo[1,5-a]pyrrolo[2,1-c][1,4]benzodiazepine-1-carboxylate of melting point 241°–242°.

EXAMPLE 10

(a) 10.6 g (50.9 mmol) of 6-nitroisatoic acid anhydride and 6.1 g (50.9 mmol) of L-proline in 70 ml of dimethyl sulphoxide are heated to 90° for 45 minutes, the mixture is subsequently evaporated in a high vacuum and the residue obtained is heated to 140° for 4 hours. The crystalline crude product is taken up in 100 ml of boiling ethanol, left to stand in the cold overnight, the material obtained is filtered off under suction while back-washing with cold ethanol and dried to constant weight. There is obtained (S)-1,2,3,11a-tetrahydro-6-nitro-5H-pyrrolo[2,1-c][1,4]benzodiazepine-5,11(10H)-dione which has a decomposition point of 235°–237°.

(b) 57.3 g (219.3 mmol) of (S)-1,2,3,11a-tetrahydro-6-nitro-5H-pyrrolo[2,1-c][1,4]benzodiazepine-5,11(10H)-dione are hydrogenated in 1.2 l of methanol with 3 g of 10% palladium/carbon at room temperature and normal pressure. After completion of the hydrogen uptake, the mixture is warmed to boiling and the catalyst is filtered off under suction, following which the filtrate is evaporated. By recrystallization from methanol there is obtained (S)-6-amino-1,2,3,11a-tetrahydro-5H-pyrrolo[2,1-c][1,4]benzodiazepine-5-11(10H)-dione of melting point 246°–248°.

(c) A suspension of 26.8 g (115.9 mmol) of (S)-6-amino-1,2,3,11a-tetrahydro-5H-pyrrolo[2,1-c][1,4]benzodiazepine-5,11(10H)-dione in 80 ml of dry dimethylformamide is treated at −20° to −10° while stirring with 5.56 g (127.4 mmol) of sodium hydride (55 percent oil dispersion), the mixture is stirred in the above temperature range for a further 1 hour and then at −45° 19 ml (127.4 mmol) of diethylchlorophosphate are added dropwise thereto.

Separately, 16.5 g (127.4 mmol) of potassium t-butylate are dissolved in 23 ml of dry dimethylformamide, cooled in an acetone/dry-ice bath, treated with 18 g (127.4 mmol) of t-butyl isocyanoacetate and the solution obtained is added dropwise at −20° to the mixture obtained according to the preceding paragraph. The mixture is left to warm to 5°, neutralized with 7.3 ml of glacial acetic acid, poured into 500 ml of water and extracted three times with methylene chloride. The methylene chloride solution is washed once with water and once with saturated sodium chloride solution, dried over magnesium sulphate and evaporated. The crude product is crystallized from ethyl acetate/diethyl ether. By recrystallization from ethyl acetate/n-hexane there is obtained t-butyl (S)-8-amino-11,12,13,13a-tetrahydro-9-oxo-9H-imidazo[1,5-a]pyrrolo[2,1-c][1,4]benzodiazepine-1-carboxylate which has a decomposition point of 223°–224°.

EXAMPLE 11

4.06 g (21.1 mmol) of about 90 percent m-chloroperbenzoic acid are dissolved in 50 ml of methylene chloride, cooled to 0°, the suspension obtained is treated portionwise with 2.5 g (7.1 mmol) of t-butyl (S)-8-amino-11,12,13,13a-tetrahydro-9-oxo-9H-imidazo[1,5-a]pyrrolo[2,1-c][1,4]benzodiazepine-1-carboxylate and stirred without cooling for a further 1 hour. The mixture is subsequently poured into about 70 ml of ice-water, made alkaline with saturated sodium bicarbonate solution, the methylene chloride solution is washed three times with saturated sodium bicarbonate solution and twice with water, dried over magnesium sulphate and evaporated. The residue obtained is chromatographed on silica gel using ethyl acetate for the elution. By recrystallization from ethyl acetate there is obtained t-butyl (S)-11,12,13,13a-tetrahydro-8-nitro-9-oxo-9H-imidazo[1,5-a]pyrrolo[2,1-c][1,4]benzodiazepine-1-carboxylate of melting point 231°–233°.

EXAMPLE 12

1.4 g (5.6 mmol) of copper sulphate pentahydrate are dissolved at 50°–60° in 5 ml of water, there are successively added dropwise thereto a solution of 0.353 g (2.8 mmol) of anhydrous sodium sulphite in 2 ml of water and 0.411 g (8.4 mmol) of sodium cyanide in 1.5 ml of water and the mixture is stirred at the above temperature for a further 10 minutes. Subsequently, the mixture is cooled in an ice-bath, the resulting precipitate is filtered off under suction while back-washing with water and it is then taken up in a solution of 0.74 g (15.1 mmol) of sodium cyanide in 3.5 ml of water.

Separately, 1.5 g (4.2 mmol) of t-butyl (S)-8-amino-11,12,13,13a-tetrahydro-9-oxo-9H-imidazo[1,5-a]pyrrolo[2,1-c][1,4]benzodiazepine-1-carboxylate are dissolved in a mixture of 1.04 ml of concentrated hydrochloric acid and 2.1 ml of water and there is added dropwise thereto at 0°–5° a solution of 0.3 g (4.3 mmol) of sodium nitrite in 1.7 ml of water. The diazonium salt solution obtained is added dropwise at 0° to the copper (I) cyanide solution obtained according to the preceding paragraph, the mixture is then warmed slowly to 70° and stirred at this temperature for a further 1 hour. Subsequently, the mixture is cooled in an ice-bath and then extracted twice with ethyl acetate. The organic extract is washed successively once with 2 N sodium hydroxide, once with water and once with saturated sodium chloride solution, dried over magnesium sulphate and evaporated. The residue obtained is chromatographed on silica gel using chloroform containing 1.5% methanol for the elution. After recrystallization from ethyl acetate, there is obtained t-butyl (S)-8-cyano-11,12,13,13a-tetrahydro-9-oxo-9H-imidazo[1,5-a]pyrrolo[2,1-c][1,4]benzodiazepine-1-carboxylate which has a decomposition point of 249°.

EXAMPLE 13

(a) 11.55 g (0.05 mol) of 6-trifluoromethylisatoic acid anhydride and 5.75 g (0.05 mol) of L-proline in 100 ml of dimethyl sulphoxide is heated to 70° for 1 hour, the solvent is removed in a high vacuum and the oil obtained is heated to 170° for 15 minutes. The crude product is purified by chromatography on silica gel using methylene chloride and mixtures of methylene chloride and ethyl acetate (5%, 10%, 15%) as the elution agent. After recrystallization of the crude product from ethyl acetate/diethyl ether, there is obtained pure (S)-1,2,3,11a-tetrahydro-6-trifluoromethyl-5H-pyrrolo[2,1-a][1,4]benzodiazepine-5,11(10H)-dione of melting point 176°–178°.

(b) A solution of 9.15 g (32.2 mmol) of (S)-1,2,3,11a-tetrahydro-6-trifluoromethyl-5H-pyrrolo[2,1-c][1,4]benzodiazepine-5,11(10H)-dione in 30 ml of dry dimethylformamide is treated at −20° to −10° while stirring with 1.54 g (35.4 mmol) of sodium hydride (55 percent oil dispersion), the mixture is stirred in the above temperature range for a further 1 hour and then at −40° 5.3 (35.4 mmol) of diethylchlorophosphate are added dropwise thereto.

Separately, 3.97 g (35.4 mmol) of potassium t-butylate are dissolved in 9 ml of dry dimethylformamide, cooled in an acetone/dry-ice bath and treated with 4.99 g (35.4 mmol) of t-butyl isocyanoacetate. The solution obtained is added dropwise at −20° to the mixture obtained according to the preceding paragraph. The mixture is left to warm to 10°, neutralized with 2.0 ml of glacial acetic acid, poured into 150 ml of water and extracted three times with methylene chloride. The methylene chloride solution is washed once with water, dried over magnesium sulphate, evaporated and the crude product obtained is chromatographed on silica gel using ethyl acetate for the elution. Subsequent crystallization from diethyl ether yields t-butyl (S)-11,12,13,13a-tetrahydro-9-oxo-8-trifluoromethyl-9H-imidazo[1,5-a]pyrrolo[2,1-c][1,4]benzodiazepine-1-carboxylate of melting point 201°–203°.

EXAMPLE 14

(a) 4-Ethylisatin is obtained from 3-ethylaniline according to the Sandmeyer isatin synthesis [T. Sandmeyer, Helv. 2, 234 (1919)]. Separation of the isomers according to P. W. Sadler, J. Org. Chemistry 21, 169 (1956), yields, after recrystallization from ethyl acetate/diethyl ether, pure 4-ethylisatin of melting point 138°–140°.

(b) 20 g (0.114 mol) of 4-ethylisatin are suspended in 75 ml of 100 percent acetic acid, treated portionwise with 26 g (0.137 mol) of m-chloroperbenzoic acid, the temperature not rising above 50°, and then the mixture is stirred at this temperature for a further 15 minutes. The mixture is poured into ice-water and filtered. The crude product obtained is taken up in ethyl acetate and extracted cautiously with a mixture of 2 N sodium hydroxide and ice. The ethyl acetate phase is dried over magnesium sulphate and concentrated to give crude 6-ethylisatoic acid anhydride which melts at 202°–204° after recrystallization from ethyl acetate.

(c) 7.65 g (0.04 mol) of 6-ethylisatoic acid anhydride and 4.6 g (0.04 mol) of L-proline are suspended in 40 ml of dimethyl sulphoxide, heated to 70° for 2.5 hours, the solvent is removed in a high vacuum and the oil obtained is heated to 170° for 15 minutes. The crude product is purified by chromatography on silica gel using chloroform for the elution. There is obtained amorphous (S)-6-ethyl-1,2,3,11a-tetrahydro-5H-pyrrolo[2,1-c][1,4]benzodiazepine-5,11(10H)-dione.

(d) A solution of 7.45 g (30.5 mmol) of (S)-6-ethyl-1,2,3,11a-tetrahydro-5H-pyrrolo[2,1-c][1,4]benzodiazepine-5,11(10H)-dione in 25 ml of dry dimethylformamide is treated at −20° C. while stirring with 1.46 g (33.55 mmol) of sodium hydride (55 percent oil dispersion), the mixture is stirred at the above temperature for 1 hour and subsequently at −45° 5.0 ml (33.55 mmol) of diethylchlorophosphate are added dropwise thereto.

Separately, 3.76 g (33.55 mmol) of potassium t-butylate are dissolved in 9 ml of dry dimethylformamide, cooled in an acetone/dry-ice bath, treated with 4.7 g (33.55 mmol) of t-butyl isocyanoacetate and the solution obtained is added dropwise at −25° to the mixture obtained according to the preceding paragraph. The mixture is stirred for 15 minutes without cooling, neutralized with 1.9 ml of glacial acetic acid, poured into 100 ml of water and extracted three times with methylene chloride. The organic extracts are washed twice with water and once with saturated sodium chloride solution, dried over magnesium sulphate and evaporated. The crude product obtained is chromatographed on silica gel using ethyl acetate containing 50% n-hexane for the elution. By recrystallization from ethyl acetate/n-hexane there is obtained t-butyl (S)-8-ethyl-11,12,13,13a-tetrahydro-9-oxo-9H-imidazo[1,5-a]pyrrolo[2,1-c][1,4]benzodiazepine-1-carboxylate of melting point 155°–156°.

EXAMPLE 15

3.37 g (30 mmol) of potassium t-butylate are dissolved in 50 ml of dimethylformamide, cooled in an acetone/dry-ice bath and 2.7 g (56 mmol) of methyl mercaptan are introduced. To this solution are added 10 g (26.75 mmol) of t-butyl (S)-8-chloro-11,12,13,13a-tetrahydro-9-oxo-9H-imidazo[1,5-a]pyrrolo[2,1-c][1,4]benzodiazepine-1-carboxylate and the mixture is then warmed to 80° for 1 hour. Subsequently, the solution is poured into 250 ml of water. The precipitated product is filtered off under suction, washed with water and dried in vacuo. There is thus obtained t-butyl (S)-11,12,13,13a-tetrahydro-8-methylthio-9-oxo-9H-imidazo[1,5-a]pyrrolo[2,1-c][1,4]benzodiazepine-1-carboxylate of melting point 236°.

EXAMPLE 16

4.0 g (10.38 mmol) of t-butyl (S)-11,12,13,13a-tetrahydro-8-methylthio-9-oxo-9H-imidazo[1,5-a]pyrrolo[2,1-c][1,4]benzodiazepine-1-carboxylate are dissolved in 25 ml of methylene chloride, treated portionwise at room temperature with 2.0 g (about 10.4 mmol) of about 90% percent m-chloroperbenzoic acid and left to stand at room temperature overnight. Then, the solution is poured into 2 N sodium hydroxide, the methylene chloride phase is separated, dried over magnesium sulphate and evaporated. After recrystallization from ethyl acetate/hexane, there is obtained t-butyl (S)-11,12,13,13a-tetrahydro-8-methylsulphinyl-9-oxo-9H-imidazo[1,5-a]pyrrolo[2,1-c][1,4]benzodiazepine-1-carboxylate of melting point 224°–225° as a diastereoisomeric mixture.

EXAMPLE 17

4 g (10.83 mmol) of t-butyl (S)-11,12,13,13a-tetrahydro-8-methylthio-9-oxo-9H-imidazo[1,5-a]pyrrolo[2,1-c][1,4]benzodiazepine-1-carboxylate are dissolved in 50 ml of methylene chloride and treated portionwise at room temperature with 4.0 g (about 20.8 mmol) of about 90 percent m-chloroperbenzoic acid. Subsequently, the mixture is warmed to boiling under reflux for 2.5 hours, then poured into 2 N sodium hydroxide and the methylene chloride solution is separated. The organic phase is dried over magnesium sulphate and evaporated. After recrystallization from chloroform/hexane, there is obtained t-butyl (S)-11,12,13,13a-tetrahydro-8-methylsulphonyl-9-oxo-9H-imidazo[1,5-a]pyrrolo[2,1-c][1,4]benzodiazepine-1-carboxylate of melting point 244°.

EXAMPLE 18

(a) 4.8 g (0.025 mmol) of 6-methoxyisatoic acid anhydride and 3.0 g (0.026 mol) of L-proline in 40 ml of dimethyl sulphoxide is heated to 70° for 2 hours, the solvent is removed in a high vacuum and the oil obtained is heated to 170° for 15 minutes. After treatment with active carbon, the crude product is recrystallized from methanol, there being obtained (S)-1,2,3,11a-tetrahydro-6-methoxy-5H-pyrrolo[2,1-c][1,4]benzodiazepine-5,11(10H)-dione of melting point 247°–251°.

(b) A suspension of 0.96 g (22 mmol) of sodium hydride (55 percent oil dispersion) in 30 ml of dry dimethylformamide is treated at −10° while stirring with 4.7 g (19.1 mmol) of (S)-1,2,3,11a-tetrahydro-6-methoxy-5H-pyrrolo[2,1-c][1,4]benzodiazepine-5,11(10H)-dione, the mixture is stirred at the above temperature for a further 50 minutes and subsequently at −35° 3.7 ml (22 mmol) of diethylchlorophosphate are added dropwise thereto.

Separately, 2.4 g (22 mmol) of potassium t-butylate are dissolved in 6.0 ml of dry dimethylformamide, cooled in an acetone/dry-ice bath, treated with 3.1 g (22 mmol) of t-butyl isocyanoacetate and the solution obtained is added dropwise at −15° to the mixture obtained according to the preceding paragraph. The mixture is stirred for a further 20 minutes without cooling, then neutralized with 1.3 ml of glacial acetic acid, poured into 80 ml of water and extracted four times with methylene chloride. The organic extracts are washed once with water, dried over magnesium sulphate and evaporated. The residue is chromatographed on silica gel using ethyl acetate containing 5% methanol for the elution. By recrystallization from ethyl acetate/n-hexane there is obtained t-butyl (S)-11,12,13,13a-tetrahydro-8-methoxy-9-oxo-9H-imidazo[1,5-a]pyrrolo[2,1-c][1,4]benzodiazepine-1-carboxylate of melting point 200°–201°.

EXAMPLE 19

A solution of 7.03 g (30 mmol) of (S)-7-fluoro-1,2,3,11a-tetrahydro-5H-pyrrolo[2,1-c][1,4]benzodiazepine-5,11(10H)-dione in 50 ml of dry dimethylformamide is treated at −25° while stirring with 1.51 g (34.5 mmol) of sodium hydride (55 percent oil dispersion), the mixture is stirred at this temperature for a further 1 hour and subsequently at −40° 5.1 ml (34.5 mmol) of diethylchlorophosphate are added dropwise thereto.

Separately, 3.86 g (34.5 mmol) of potassium t-butylate are dissolved in 10 ml of dry dimethylformamide, cooled in an acetone/dry-ice bath, treated with 4.86 g (34.5 mmol) of t-butyl isocyanoacetate and the solution obtained is added dropwise at −15° to the mixture obtained according to the preceding paragraph. The mixture is left to warm to 5°, neutralized with 3.9 ml of glacial acetic acid, poured into 250 ml of water and extracted three times with methylene chloride. The organic extracts are washed twice with water, dried over magnesium sulphate and evaporated. The crude product obtained is chromatographed on silica gel using ethyl acetate for the elution. After recrystallization from ethanol, there is obtained t-butyl (S)-7-fluoro-11,12,13,13a-tetrahydro-9-oxo-9H-imidazo[1,5-a]pyrrolo[2,1-c][1,4]benzodiazepine-1-carboxylate of melting point 154°–155°.

EXAMPLE 20

(a) 4-chloro-5-fluoroisatin is obtained from 3-chloro-4-fluoroaniline according to the Sandmeyer isatin synthesis [T. Sandmeyer, Helv. 2, 234 (1919)]. Separation of the isomers according to P. W. Sadler, J. Org. Chemistry 21, 169 (1956) yields, after recrystallization, pure 4-chloro-5-fluoroisatin of melting point 249°–251°.

(b) 7.8 g (0.039 mol) of 4-chloro-5-fluoroisatin are suspended in 50 ml of 100 percent acetic acid, treated with 0.25 ml of concentrated sulphuric acid and then at 30° 4.4 ml (0.043 mol) of 30 percent hydrogen peroxide are added thereto. The mixture is subsequently heated to 70° for 2.5 hours, then cooled to 10° and filtered. The crude product is recrystallized from acetone/hexane, there being obtained 6-chloro-5-fluoroisatoic acid anhydride of melting point 275°–278° (decomposition).

(c) 3.3 g (0.015 mol) of 6-chloro-5-fluoroisatoic acid anhydride and 2 g (0.017 mol) of L-proline in 7.5 ml of dimethylformamide are heated to 120° for 2 hours, cooled, treated with 12 ml of distilled water and the precipitated brown crystals are filtered off. By recrystallization of the crude product from acetone/hexane there is obtained (S)-6-chloro-7-fluoro-1,2,3,11a-tetrahydro-5H-pyrrolo[2,1-c][1,4]benzodiazepine-5,11(10H)-dione of melting point 217°–219°.

(d) A solution of 7.16 g (26.6 mmol) of (S)-6-chloro-7-fluoro-1,2,3,11a-tetrahydro-5H-pyrrolo[2,1-c][1,4]benzodiazepine-5,11(10H)-dione in 25 ml of dry dimethylformamide is treated at −20° to −10° while stirring with 1.27 g (29.26 mmol) of sodium hydride (55 percent oil dispersion), the mixture is stirred in the above temperature range for a further 1.25 hours and then at −40° 4.4 ml (29.26 mmol) of diethylchlorophosphate are added dropwise thereto.

Separately, 3.28 g (29.3 mmol) of potassium t-butylate are dissolved in 8 ml of dry dimethylformamide, cooled in an acetone/dry-ice bath, treated with 4.13 g (29.3 mmol) of t-butyl isocyanoacetate and the solution obtained is added dropwise at −20° to −10° to the mixture obtained according to the preceding paragraph. The mixture is left to warm to 10°, neutralized with 1.7 ml of glacial acetic acid, poured into 150 ml of water and extracted three times with methylene chloride. The methylene chloride solution is washed once with water, dried over magnesium sulphate and evaporated. The crude product obtained is chromatographed on silica gel using ethyl acetate for the elution. By crystallization from diethyl ether there is obtained t-butyl (S)-8-chloro-7-fluoro-11,12,13,13a-tetrahydro-9-oxo-9H-imidazo[1,5-a]pyrrolo[2,1-c][1,4]benzodiazepine-1-carboxylate of melting point 211°–212°.

EXAMPLE 21

(a) 37.0 g (187.3 mmol) of 6-chloroisatoic acid anhydride and 24.6 g (187.3 mmol) of L-4-hydroxyproline in 180 ml of dimethyl sulphoxide is heated to 100° for 2 hours, evaporated to dryness in a high vacuum and the residue obtained is heated to 130° for 2 hours. By recrystallization from ethanol there is obtained (2R,11aS)-6-chloro-1,2,3,11a-tetrahydro-2-hydroxy-5H-pyrrolo[2,1-c][1,4]benzodiazepine-5,11(10H)-dione of melting point 284°–287°.

(b) A suspension of 4.0 g (15 mmol) of (2R,11aS)-6-chloro-1,2,3,11a-tetrahydro-2-hydroxy-5H-pyrrolo[2,1-c][1,4]benzodiazepine-5,11(10H)-dione in 20 ml of pyridine is treated while stirring with 1.4 ml (18 mmol) of methanesulphonyl chloride, the mixture is stirred at room temperature for a further 1.25 hours, the solution is evaporated and the residue is partitioned between 100 ml of chloroform and 70 ml of water. The chloroform solution is washed twice with water, dried over magnesium sulphate and evaporated. By crystallization of the resulting residue from ethanol there is obtained (2R,11aS)-6-chloro-2,3,5,10,11,11a-hexahydro-5,11-dioxo-1H pyrrolo[2,1-c][1,4]benzodiazepin-2-yl-methanesulphonate of melting point 213°–215°.

(c) A solution of 17.0 g (49.3 mmol) of (2R,11aS)-6-chloro-2,3,5,10,11,11a-hexahydro-5,11-dioxo-1H-pyrrolo[2,1-c][1,4]benzodiazepin-2-yl-methanesulphonate in 80 ml of dry dimethylformamide is treated with 4.3 g (98.6 mmol) of sodium hydride (55 percent oil dispersion), the mixture is stirred at 45° for a further 2 hours, then poured into 300 ml of ice-water, neutralized with 5.6 ml of glacial acetic acid and extracted four times with methylene chloride. The organic extracts are washed once with saturated sodium chloride solution, dried over magnesium sulphate and evaporated. By crystallization from ethanol there is obtained (S)-6-chloro-1,11a-dihydro-5H-pyrrolo[2,1-c][1,4]benzodiazepine-5,11(10H)-dione of melting point 249°–251°.

(d) A solution of 8.59 g (34.5 mmol) of (S)-6-chloro-1,11a-dihydro-5H-pyrrolo[2,1-c][1,4]benzodiazepine-5,11(10H)-dione in 35 ml of dry dimethylformamide is treated at −20° to −10° while stirring with 1.66 g (38 mmol) of sodium hydride (55 percent oil dispersion), the mixture is stirred in the above temperature range for a further 1 hour and subsequently at −40°5.5 ml (38 mmol) of diethylchlorophosphate are added dropwise thereto.

Separately, 4.3 g (38 mmol) of potassium t-butylate are dissolved in 7 ml of dry dimethylformamide, cooled in an acetone/dry-ice bath, treated with 6.0 g (38 mmol) of about 90 percent t-butyl isocyanoacetate and the solution obtained is added dropwise at −20° to the mixture obtained according to the preceding paragraph. The mixture is left to warm to 10°, neutralized with 2.2 ml of glacial acetic acid, poured into 200 ml of water and extracted four times with methylene chloride. The methylene chloride solution is washed once with water, dried over magnesium sulphate and evaporated. The residue is dissolved in hot ethyl acetate, left to stand in a refrigerator overnight and the precipitated material is filtered off under suction while back-washing with cold ethyl acetate. Recrystallization of the crude product from ethanol yields t-butyl (S)-8-chloro-13,13a-dihydro-9-oxo-9H-imidazo[1,5-a]pyrrolo[2,1-c][1,4]benzodiazepine-1-carboxylate of melting point 235°–237°.

EXAMPLE 22

(a) 13.0 g (128.4 mmol) of L-azetidine-2-carboxylic acid and 22.7 g (128.4 mmol) of 6-methylisatoic acid anhydride in 150 ml of dimethyl sulphoxide are heated to 95° for 3 hours, evaporated to dryness in a high vacuum and the residue obtained is heated to 140° for 2.25 hours. By crystallization from ethyl acetate there is obtained (S)-1,10a-dihydro-5-methyl-2H-azeto[2,1-c][1,4]benzodiazepine-4,10(9H)-dione of melting point 159°–160°.

(b) A solution of 13.8 g (63.8 mmol) of (S)-1,10a-dihydro-5-methyl-2H-azeto[2,1c][1,4]benzodiazepine-4,10-(9H)-dione in 55 ml of dry dimethylformamide is treated at −20° to −10° while stirring with 3.06 g (70.2 mmol) of sodium hydride (55 percent oil dispersion), the mixture is stirred at the above temperature for a further 40 minutes and subsequently at −35° 10.5 ml (70.2 mmol) of diethylchlorophosphate are added dropwise thereto.

Separately, 7.88 g (70.2 mmol) of potassium t-butylate are dissolved in 12 ml of dry dimethylformamide, cooled in an acetone/dry-ice bath, treated with 11 g (70.2 mmol) of about 90 percent t-butyl isocyanoacetate and the solution obtained is added dropwise at −20° to −15° to the mixture obtained according to the preceding paragraph. The mixture is left to warm to 0°, neutralized with 4 ml of glacial acetic acid, poured into 300 ml of water and extracted three times with methylene chloride. The methylene chloride solution is washed twice with water, dried over magnesium sulphate and evaporated. The crude product obtained is chromatographed on silica gel using ethyl acetate containing 50% n-hexane for the elution. After recrystallization from ethyl acetate/n-hexane, there is obtained t-butyl (S)-12,12a-dihydro-8-methyl-9-oxo-9H,11H-azeto[2,1-c]imidazo[1,5-a][1,4]benzodiazepine-1-carboxylate of melting point 191°–192°.

EXAMPLE 23

11.0 g (47.5 mmol) of 6-trifluoromethylisatoic acid anhydride and 4.8 g (47.5 mmol) of L-azetidine-2-carboxylic acid in 50 ml of dimethyl sulphoxide are heated to 105° for 45 minutes. Subsequently, the mixture is evaporated to dryness in a high vacuum and the residue obtained is heated to 150° for 2 hours. The crude product is purified by chromatography on silica gel using methylene chloride containing 7% ethyl acetate for the elution.

7.3 g of the oil obtained are taken up in 30 ml of dry dimethylformamide, the solution is treated at −20° with 1.26 g (29 mmol) of sodium hydride (55 percent oil dispersion), the mixture is stirred at the above temperature for a further 50 minutes and then at −25° there is added dropwise thereto a solution of 7.38 g (29 mmol) of dimorpholinophosphonic acid chloride in 10 ml of dry dimethylformamide.

Separately, 3.25 g (29 mmol) of potassium t-butylate are dissolved in 8 ml of dry dimethylformamide, cooled in an acetone/dry-ice bath, treated with 4.09 g (29 mmol) of t-butyl isocyanoacetate and the solution obtained is added dropwise at −20° to the mixture obtained according to the preceding paragraph. The mixture is stirred for a further 20 hours without cooling, neutralized with 1.6 ml of glacial acetic acid, poured into 100 ml of water and extracted four times with methylene chloride. The methylene chloride solution is washed once with water and once with saturated sodium chloride solution, dried over magnesium sulphate and evaporated. The crude product obtained is chromatographed on silica gel using ethyl acetate/n-hexane (3:2) and ethyl acetate for the elution. By recrystallization from ethyl acetate there is obtained t-butyl (S)-12,12a-dihydro-9-oxo-8-trifluoromethyl-9H,11H-azeto[2,1-c]imidazo[1,5-a][1,4]benzodiazepine-1-carboxylate which has a decomposition point of 217°–219°.

EXAMPLE 24

(a) 36 g (0.26 mol) of 3-aminopyridine-2-carboxylic acid, 46.6 g (0.29 mol) of N,N'-carbonyldiimidazole and 200 ml of dimethylformamide are stirred at room temperature until the carbon dioxide evolution has finished, then the mixture is treated with 26.3 g (0.26 mol) of triethylamine and 43.1 g (0.26 mol) of methyl L-prolinate and stirred at room temperature for a further 1.5 hours. Subsequently, the solution is poured into water, extracted four times with chloroform, the combined chloroform extracts are dried over magnesium sulphate and then evaporated in vacuo. The oily residue is treated with 500 ml of glacial acetic acid, heated to boiling under reflux for 1 hour and then evaporated to dryness. By recrystallization from ethanol there is obtained 6a,7,8,9-tetrahydro-6H-pyrido[3,2-e]pyrrolo[1,2-a][1,4]diazepine-6,11(5H)-dione of melting point 249°–250°.

(b) A solution of 6.33 g (29.1 mmol) of 6a,7,8,9-tetrahydro-6H-pyrido[3,2-e]pyrrolo[1,2-a][1,4]diazepine-6,11(5H)-dione in 20 ml of dry dimethylformamide is treated at 0° while stirring with 1.4 g (29.1 mmol) of sodium hydride (50 percent oil dispersion), the mixture is stirred at the above temperature for a further 1 hour and then at −30° 4.2 ml (29.1 mmol) of diethylchlorophosphate are added dropwise thereto.

Separately, 3.3 g (29.1 mmol) of potassium t-butylate are dissolved in 5 ml of dry dimethylformamide, cooled in an acetone/dry-ice bath, treated with 4.1 g (29.1 mmol) of t-butyl isocyanoacetate and the solution obtained is added dropwise at −20° to −10° to the mixture obtained according to the preceding paragraph. The mixture is stirred for a further 1 hour without cooling, then neutralized with 1.7 ml of glacial acetic acid, poured into 200 ml of water and extracted three times with chloroform. The chloroform solution is washed three times with water, dried over magnesium sulphate and evaporated. The residue obtained is chromatographed on silica gel using chloroform/methanol (9:1) for the elution and the material obtained is subsequently recrystallized from ethyl acetate. There is obtained t-butyl 11,12,13,13a-tetrahydro-9-oxo-9H-imidazo[5,1-c]pyrido[3,2-e]pyrrolo[1,2-a][1,4]diazepine-1-carboxylate of melting point 230°–231°.

EXAMPLE 25

(a) 13.8 g (0.1 mol) of 4-aminopyridine-3-carboxylic acid, 24.3 g (0.15 mol) of N,N'-carbonyldiimidazole and 130 ml of dimethylformamide are heated to 55° for 4 hours, the solution obtained is treated with 10.2 g of triethylamine and 16.5 g (0.1 mol) of methyl L-prolinate hydrochloride, heated to 85° for a further 3 hours and then evaporated in a high vacuum. 125 ml of glacial acetic acid are added to the residue, mixture is heated to boiling under reflux for 0.5 hour and evaporated. The residue is taken up in chloroform, the solution obtained is washed with water, dried over magnesium sulphate and evaporated. By chromatography on silica gel using ethyl acetate/methanol for the elution there is obtained (S)-6a,7,8,9-tetrahydro-6H-pyrido[4,3-a]pyrrolo[1,2-a][1,4]diazepine-6,11(5H)dione of melting point 266°–268°.

(b) A solution of 7.15 g (33 mmol) of (S)-6a,7,8,9-tetrahydro-6H-pyrido[4,3-e]pyrrolo[1,2-a][1,4]diazepine-6,11(5H)-dione in 30 ml of dry dimethylformamide is treated at −10° while stirring with 1.53 g (35 mmol) of sodium hydride (55 percent oil dispersion), the mixture is stirred at the above temperature for a further 30 minutes and then at −30° 5 ml (35 mmol) of diethylchlorophosphate are added dropwise thereto.

Separately, 3.92 g (35 mmol) of potassium t-butylate are dissolved in 6 ml of dry dimethylformamide, cooled in an acetone/dry-ice bath, treated with 4.8 g (34 mmol) of t-butyl isocyanoacetate and the solution obtained is added dropwise at −20° to −10° to the mixture obtained according to the preceding paragraph. The mixture is left to warm to room temperature, neutralized with 3.5 ml of glacial acetic acid, poured into 300 ml of water and extracted three times with chloroform. The organic extracts are washed three times with water, dried over magnesium sulphate and evaporated. By crystallization from ethyl acetate there is obtained t-butyl 11,12,13,13a-tetrahydro-9-oxo-9H-imidazo[5,1-c]pyrido[4,3-e]pyrrolo[1,2-a][1,4]-diazepine-1-carboxylate of melting point 217°–218°.

EXAMPLE 26

(a) 15 g (43.4 mmol) of ethyl (S)-8-chloro-11,12,13,13a-tetrahydro-9-oxo-9H-imidazo[1,5-a]pyrrolo[2,1-c][1,4]benzodiazepine-1-carboxylate and 1.85 g (46.3 mmol) of sodium hydroxide are treated with 60 ml of ethanol and 10 ml of water, then heated to boiling under reflux for 45 minutes, the ethanol is subsequently distilled off in vacuo, the residue is treated with 46.5 ml of 1 N hydrochloric acid and left to stand in an ice-bath for 2 hours. The precipitated material is filtered off under suction, washed with water and dried to constant weight. There is obtained (S)-8-chloro-11,12,13,13a-tetrahydro-9-oxo-9H-imidazo[1,5-a]pyrrolo[2,1-c][1,4]benzodiazepine-1-carboxylic acid which has a decomposition point of 265°.

(b) 9.54 g (30 mmol) of (S)-8-chloro-11,12,13,13a-tetrahydro-9-oxo-9H-imidazo[1,5-a]pyrrolo[2,1-c][1,4]benzodiazepine-1-carboxylic acid and 6.32 g (39 mmol) of N,N'-carbonyldiimidazole in 50 ml of dry dimethylformamide are stirred at room temperature for 1 hour and at 50° for 1 hour. Subsequently, the mixture is poured into about 300 ml of water, the precipitated material is filtered off under suction, washed with water and dried to constant weight. There is obtained (S)-1-[(8-chloro-11,12,13,13a-tetrahydro-9-oxo-9H-imidazo[1,5-a]pyrrolo[2,1-c][1,4]benzodiazepin-1-yl)carbonyl]imidazole of melting point 240°–241.5°.

(c) A suspension of 1.1 g (3 mmol) of (S)-1-[(8-chloro-11,12,13,13a-tetrahydro-9-oxo-9H-imidazo[1,5-a]pyrrolo[2,1-c][1,4]benzodiazepin-1-yl)carbonyl]imidazole in 10 ml of dry dimethylformamide is treated while stirring with 0.34 g (3 mmol) of potassium t-butylate, the mixture is stirred at room temperature for a further 30 minutes, then poured into 200 ml of water and extracted three times with chloroform. The chloroform solution is washed three times with water, dried over magnesium sulphate and evaporated. After crystallization from ethyl acetate, there is obtained t-butyl 8-chloro-11,12,13,13a-tetrahydro-9-oxo-9H-imidazo[1,5-a]pyrrolo[2,1-c][1,4]benzodiazepine-1-carboxylate of melting point 223°–225°.

EXAMPLE 27

(a) 57.3 g (219 mmol) of (S)-1,2,3,11a-tetrahydro-7-nitro-5H-pyrrolo[2,1-c][1,4]benzodiazepine-5,11(10H)-dione are hydrogenated in 1.3 l of methanol over 3 g of 10 percent palladium/carbon at room temperature and normal pressure. After completion of the hydrogen uptake, the catalyst is filtered off under suction, the filtrate is evaporated in vacuo and the residue obtained is recrystallized from isopropanol. There is thus obtained (S)-7-amino-1,2,3,11a-tetrahydro-5H-pyrrolo[2,1-c][1,4]benzodiazepine-5,11(10H)-dione of melting point 237.5°–238.5°.

(b) A solution of 4.61 g (20 mmol) of (S)-7-amino-1,2,3,11a-tetrahydro-5H-pyrrolo[2,1-c][1,4]benzodiazepine-5,11(10H)-dione in 25 ml of dry dimethylformamide is treated while stirring and cooling with ice/methanol with 0.96 g (20 mmol) of sodium hydride (55 percent oil dispersion), the mixture is then stirred at room temperature for a further 20 minutes and subsequently there is added dropwise thereto at −30° a solution of 5.1 g (20 mmol) of dimorpholinophosphonic acid chloride in 15 ml of dry dimethylformamide.

Separately, 2.47 g (20 mmol) of potassium t-butylate are dissolved in 5 ml of dry dimethylformamide, cooled in an acetone/dry-ice bath, treated with 2.82 g (20 mmol) of t-butyl isocyanoacetate and the solution obtained is added dropwise at −20° to the mixture obtained according to the preceding paragraph. The mixture is stirred for a further 30 minutes without cooling, neutralized with 1.1 ml of glacial acetic acid, poured into 300 ml of water and extracted three times with chloroform. The chloroform solution is washed three times with water, dried over magnesium sulphate and evaporated. The residue obtained is chromatographed on silica gel using chloroform containing 3.6% methanol for the elution. By crystallization of the material obtained from ethyl acetate there is obtained t-butyl (S)-7-amino-11,12,13,13a-tetrahydro-9-oxo-9H-imidazo[1,5-a]pyrrolo[2,1-c][1,4]benzodiazepine-1-carboxylate of melting point 223°–224°.

EXAMPLE 28

1.5 g (4.2 mmol) of t-butyl (S)-7-amino-11,12,13,13a-tetrahydro-9-oxo-9H-imidazo[1,5-a]pyrrolo[2,1-c][1,4]benzodiazepine-1-carboxylate and 0.783 g (4.4 mmol) of N-bromosuccinimide in 15 ml of dimethylformamide are stirred at room temperature for 45 minutes, subsequently poured into 250 ml of water and extracted three times with chloroform. The chloroform solution is washed three times with water, dried over magnesium sulphate and evaporated. The residue obtained is chromatographed on silica gel using chloroform containing 4% methanol for the elution. Recrystallization of the material obtained from ethyl acetate yields t-butyl (S)-7-amino-8-bromo-11,12,13,13a-tetrahydro-9-oxo-9H-imidazo[1,5-a]pyrrolo[2,1-c][1,4]benzodiazepine-1-carboxylate of melting point 245°–246°.

EXAMPLE 29

380 mg (0.9 mmol) of t-butyl (S)-7-amino-8-bromo-11,12,13,13a-tetrahydro-9-oxo-9H-imidazo[1,5-a]pyrrolo[2,1-c][1,4]benzodiazepine-1-carboxylate and 109 mg (1.05 mmol) of t-butyl nitrite in 10 ml of tetrahydrofuran are heated to boiling under reflux overnight and subsequently evaporated to dryness in vacuo. The residue obtained is chromatographed on silica gel using ethyl acetate for the elution. By crystallization from ethyl acetate there is finally obtained t-butyl (S)-8-bromo-11,12,13,13a-tetrahydro-9-oxo-9H-imidazo[1,5-a]pyrrolo[2,1-c][1,4]benzodiazepine-1-carboxylate of melting point 204°–205°.

t-Butyl (S)-8-chloro-11,12,13,13a-tetrahydro-9-oxo-9H-imidazo[1,5-a]pyrrolo[2,1-c][1,4]benzodiazepine-1-carboxylate can be used as the active substance for the manufacture of pharmaceutical preparations as illustrated in Examples A to C hereinafter:

EXAMPLE A

Tablets containing the following ingredients are manufactured in the usual manner:

| | mg/tablet |
|---|---|
| Active substance | 5 |
| Lactose | 45 |
| Maize starch | 15 |
| Microcrystalline cellulose | 34 |
| Magnesium stearate | 1 |
| Tablet weight | 100 |

EXAMPLE B

Capsules containing the following ingredients are manufactured:

| | mg/capsule |
|---|---|
| Active substance | 10 |
| Lactose | 155 |
| Maize starch | 30 |
| Talc | 5 |
| Capsule fill weight | 200 |

The active substance, the lactose and the maize starch are firstly mixed in a mixer and then in a comminuting machine. The mixture is returned to the mixer, the talc is added thereto and mixed thoroughly, The mixture is filled by machine into hard gelatine capsules.

EXAMPLE C

Suppositories containing the following ingredients are manufactured:

| | mg/supp. |
|---|---|
| Active substance | 15 |
| Suppository substance | 1285 |
| Total | 1300 |

The suppository substance is melted in a glass or steel vessel, mixed thoroughly and cooled to 45°. Thereupon, there is added thereto the finely powdered active substance and the mixture is stirred until it is completely dispersed. The mixture is poured into suppository moulds of suitable size, left to cool, the suppositories are then removed from the moulds and packed individually in wax paper or metal foil.

The compounds of formula I listed hereinafter can be used as the active substance in Examples A to C hereinbefore in place of t-butyl (S)-8-chloro-11,12,13,13a-tetrahydro-9-oxo-9H-imidazo[1,5-a]pyrrolo[2,1-c][1,4]benzodiazepine-1-carboxylate:

t-Butyl (S)-8-chloro-12,12a-dihydro-9-oxo-9H,11H-azeto[2,1-c]imidazo[1,5-a][1,4]benzodiazepine-1-carboxylate,
t-butyl (S)-11,12,13,13a-tetrahydro-8-methyl-9-oxo-9H-imidazo[1,5-a]pyrrolo[2,1-c][1,4]benzodiazepine-1-carboxylate,
t-butyl (S)-8-bromo-11,12,13,13a-tetrahydro-9-oxo-9H-imidazo[1,5-a]pyrrolo[2,1-c][1,4]benzodiazepine-1-carboxylate,
t-butyl (S)-11,12,13,13a-tetrahydro-8-iodo-9-oxo-9H-imidazo[1,5-c]pyrrolo[2,1-c][1,4]benzodiazepine-1-carboxylate,
t-butyl (S)-11,12,13,13a-tetrahydro-9-oxo-8-trifluoromethyl-9H-imidazo[1,5-a]pyrrolo[2,1-c][1,4]benzodiazepine-1-carboxylate,
t-butyl (S)-8-ethyl-11,12,13,13a-tetrahydro-9-oxo-9H-imidazo[1,5-a]pyrrolo[2,1-c][1,4]benzodiazepine-1-carboxylate,
t-butyl (S)-8-chloro-7-fluoro-11,12,13,13a-tetrahydro-9-oxo-9H-imidazo[1,5-a]pyrrolo[2,1-c][1,4]benzodiazepine-1-carboxylate,
t-butyl (S)-12,12a-dihydro-8-methyl-9-oxo-9H,11H-azeto[2,1-c]imidazo[1,5-a][1,4]benzodiazepine-1-carboxylate and
t-butyl (S)-12,12a-dihydro-9-oxo-8-trifluoromethyl-9H,11H-azeto[2,1-c]imidazo[1,5-a][1,4]benzodiazepine-1-carboxylate.

What is claimed:

1. A compound of the formula $$\text{Formula I}$$

with substituent $COOC(CH_3)_3$, containing ring atoms labeled $\alpha$, $\beta$, $\gamma$, with groups A and B, and a C=O linkage to N.

wherein A together with the two carbon atoms denoted as $\alpha$ and $\beta$ is the group (a) a benzene ring bearing $R^1$ and $R^2$ substituents, with positions $\alpha$ and $\beta$, (b) a pyridine-type ring with N, and positions $\alpha$ and $\beta$, (c) a pyridine-type ring with N, and positions $\alpha$ and $\beta$, or (d) a thiophene ring with S, and positions $\alpha$ and $\beta$, B is dimethylene, trimethylene or propenylene, $R^1$ is hydrogen, halogen, trifluoromethyl, amino, nitro, cyano or lower alkyl and $R^2$ is hydrogen, halogen, trifluoromethyl, amino, nitro, cyano, lower alkyl, lower alkoxy, lower alkylthio, lower alkylsulphinyl or lower alkylsulphonyl, and the carbon atom denoted as $\gamma$ has the (S)— or (R,S)—configuration, and pharmaceutically acceptable acid addition salts thereof.

2. The compound of claim 1, wherein A is the group (a), one of $R^1$ and $R^2$ is hydrogen and the other is nitro or cyano and B is dimethylene, trimethylene or propenylene, and the carbon atom denoted as $\gamma$ has the (S)— or (R,S)—configuration.

3. The compound of claim 1, wherein A is the group (a) or (d), B is dimethylene, $R^1$ is hydrogen, halogen or trifluoromethyl and $R^2$ is hydrogen, halogen, trifluoromethyl or lower alkyl, and the carbon atom denoted as γ has the (S)— or (R,S)—configuration.

4. The compound of claim 1, wherein A is the group (a) or (d), B is trimethylene or propenylene, $R^1$ is hydrogen, halogen or trifluoromethyl and $R^2$ is hydrogen, halogen, trifluoromethyl or lower alkyl, and the carbon atom denoted as γ has the (S)— or (R,S)—configuration.

5. The compound of claim 1, wherein A is the group (b) or (c) and B is dimethylene, trimethylene or propenylene, and the carbon atom denoted as γ has the (S)— or (R,S)—configuration.

6. The compound of claim 1, wherein A is the group (a), B is dimethylene, trimethylene or propenylene and either $R^1$ is lower alkyl and $R^2$ is hydrogen, halogen, trifluoromethyl, nitro, cyano or lower alkyl or one of $R^1$ and $R^2$ is nitro or cyano and the other is halogen, trifluoromethyl, nitro, cyano or lower alkyl, and the carbon atom denoted as γ has the (S)— or (R,S)—configuration.

7. The compound of claim 1, wherein A is the group (a), (b), (c) or (d), $R^1$ is hydrogen, amino or halogen and $R^2$ is hydrogen, halogen, trifluoromethyl, lower alkyl, cyano, nitro, amino, lower alkoxy, lower alkylthio, lower alkylsulphinyl or lower alkylsulphonyl.

8. The compound of claim 7, wherein $R^1$ is hydrogen or halogen and $R^2$ is halogen, trifluoromethyl or lower alkyl.

9. The compound of claim 8, wherein B is dimethylene or trimethylene.

10. The compound of claim 9, wherein the carbon atom denoted as γ has the (S)—configuration.

11. The compound: t-Butyl(S)-12,12a-dihydro-9-oxo-8-trifluoromethyl-9H,11H-azeto [2,1-c]imidazo[1,5-a][1,4]benzodiazepine-1-carboxylate.

12. The compound: t-Butyl (S)-12,12a-dihydro-8-methyl-9-oxo-9H,11H-azeto[2,1-c]imidazo[1,5-a][1,4]benzodiazepine-1-carboxylate.

13. The compound: t-Butyl (S)-8-chloro-7-fluoro-11,12,13,13a-tetrahydro-9-oxo-9H-imidazo[1,5-a]pyrrolo[2,1-c][1,4]benzodiazepine-1-carboxylate.

14. The compound: t-Butyl (S)-8-chloro-11,12,13,13a-tetrahydro-9-oxo-9H-imidazo[1,5-a]pyrrolo[2,1-c][1,4]benzodiazepine-1-carboxylate.

15. The compound: t-Butyl (S)-8-ethyl-11,12,13,13a-tetrahydro-9-oxo-9H-imidazo [1,5-a]pyrrolo[2,1-c][1,4]benzodiazepine-1-carboxylate.

16. The compound: t-Butyl (S)-11,12,13,13a-tetrahydro-9-oxo-8-trifluoromethyl-9H-imidazo[1,5-a]pyrrolo[2,1-c][1,4]-benzodiazepine-1-carboxylate.

17. The compound: t-Butyl (S)-8-bromo-11,12,13,13a-tetrahydro-9-oxo-9H-imidazo[1,5-a]pyrrolo[2,1-c][1,4]benzodiazepine-1-carboxylate.

18. The compound: t-Butyl (S)-11,12,13,13a-tetrahydro-8-iodo-9-oxo-9H-imidazo[1,5-a]pyrrolo[2,1-c][1,4]benzodiazepine-1-carboxylate.

19. The compound: t-Butyl (S)-8-chloro-12,12a-dihydro-9-oxo-9H,11H-azeto[2,1-c]imidazo[1,5-a][1,4]benzodiazepine-1-carboxylate.

20. The compound: t-Butyl (S)-11,12,13,13a-tetrahydro-8-methyl-9-oxo-9H-imidazo[1,5-a]pyrrolo[2,1-c][1,4]benzodiazepine-1-carboxylate.

21. A compound selected from the group consisting of t-Butyl 8-chloro-11,13a-dihydro-9-oxo-9H-imidazo-[1,5a]pyrrolo[2,1-c][1,4]benzodiazepine-1-carboxylate, t-butyl (S)-10,11,12,12a-tetrahydro-8-oxo-8H-imidazo-[5,1-c]pyrrolo[1,2-a]thieno[3,2-e][1,4]diazepine-1-carboxylate, t-butyl (S)-11,12,13,13a-tetrahydro-9-oxo-9H-imidazo[1,5-a]pyrrolo[2,1-c][1,4]benzodiazepine-1-carboxylate, t-butyl (S)-7-chloro-11,12,13,13a-tetrahydro-9-oxo-9H-imidazo[1,5-a]pyrrolo[2,1-c][1,4]benzodiazepine-1-carboxylate, t-butyl (S)-8-amino-11,12,13,13a-tetrahydro-9-oxo-9H-imidazo[1,5-a]pyrrolo[2,1-c][1,4]benzodiazepine-1-carboxylate, t-butyl (S)-11,12,13,13a-tetrahydro-8-nitro-9-oxo-9H-imidazo[1,5-a]pyrrolo[2,1-c][1,4]benzodiazepine-1-carboxylate, t-butyl (S)-8-cyano-11,12,13,13a-tetrahydro-9-oxo-9H-imidazo[1,5-a]pyrrolo[2,1-c][1,4]benzodiazepine-1-carboxylate, t-butyl (S)-11,12,13,13a-tetrahydro-8-methylthio-9-oxo-9H-imidazo[1,5-a]pyrrolo[2,1-c][1,4]benzodiazepine-1-carboxylate, t-butyl (S)-11,12,13,13a-tetrahydro-8-methylsulphonyl-9-oxo-9H-imidazo[1,5-a]pyrrolo[2,1-c][1,4]benzodiazepine-1-carboxylate, t-butyl (S)-7-fluoro-11,12,13,13a-tetrahydro-9-oxo-9H-imidazo[1,5-a]pyrrolo[2,1-c][1,4]benzodiazepine-1-carboxylate and t-butyl (S)-8-chloro-13,13a-dihydro-9-oxo-9H-imidazo[1,5-a]pyrrolo[2,1-c][1,4]benzodiazepine-1-carboxylate.

* * * * *